US010842628B1

(12) United States Patent
Pesce et al.

(10) Patent No.: US 10,842,628 B1
(45) Date of Patent: Nov. 24, 2020

(54) HEART VALVE SUPPORT DEVICE

(71) Applicant: TriFlo Cardiovascular Inc., Huntington Beach, CA (US)

(72) Inventors: Luca Pesce, Huntington Beach, CA (US); John Paul Ussia, Huntington Beach, CA (US); Christine Thanh Nguyen, Huntington Beach, CA (US); Christine Thao Nguyen, Huntington Beach, CA (US)

(73) Assignee: TriFlo Cardiovascular Inc., Huntington Beach, CA (US)

( * ) Notice: Subject to any disclaimer, the term of this patent is extended or adjusted under 35 U.S.C. 154(b) by 0 days.

(21) Appl. No.: 16/882,226

(22) Filed: May 22, 2020

Related U.S. Application Data

(60) Provisional application No. 62/851,503, filed on May 22, 2019, provisional application No. 62/976,232, filed on Feb. 13, 2020.

(51) Int. Cl.
A61F 2/24 (2006.01)

(52) U.S. Cl.
CPC ............ *A61F 2/246* (2013.01); *A61F 2/2418* (2013.01); *A61F 2/2469* (2013.01); *A61F 2210/0014* (2013.01); *A61F 2220/0025* (2013.01); *A61F 2230/0071* (2013.01)

(58) Field of Classification Search
CPC ....... A61F 2/2418; A61F 2/246; A61F 2/2469
See application file for complete search history.

(56) References Cited

U.S. PATENT DOCUMENTS

| 5,954,766 | A  | 9/1999  | Zadno Azizi et al. |
| 6,048,189 | A  | 4/2000  | Kurihara et al. |
| 6,764,510 | B2 | 7/2004  | Vidlund et al. |
| 6,797,002 | B2 | 9/2004  | Spence et al. |
| 6,848,440 | B2 | 2/2005  | Han et al. |
| 7,611,534 | B2 | 11/2009 | Kapadia et al. |
| 7,704,277 | B2 | 4/2010  | Zakay et al. |
| 7,854,762 | B2 | 12/2010 | Speziali et al. |
| 8,092,525 | B2 | 1/2012  | Eliasen et al. |
| 8,109,996 | B2 | 2/2012  | Stacchino et al. |
| 8,377,115 | B2 | 2/2013  | Thompson |
| 8,475,525 | B2 | 7/2013  | Maisano et al. |
| 8,597,347 | B2 | 12/2013 | Maurer et al. |
| 8,778,017 | B2 | 7/2014  | Eliasen et al. |
| 8,961,596 | B2 | 2/2015  | Maisano et al. |
| 9,241,702 | B2 | 1/2016  | Maisano et al. |
| 9,307,980 | B2 | 4/2016  | Gilmore et al. |
| 9,414,918 | B2 | 8/2016  | Chau et al. |
| 9,474,605 | B2 | 10/2016 | Rowe et al. |
| 9,629,720 | B2 | 4/2017  | Nguyen et al. |

(Continued)

FOREIGN PATENT DOCUMENTS

| WO | WO2008/141325 A1 | 11/2008 |
| WO | WO2013/173587 A1 | 11/2013 |
| WO | WO20161180529 A1 | 11/2016 |

*Primary Examiner* — Suba Ganesan
(74) *Attorney, Agent, or Firm* — Shay Glenn LLP

(57) ABSTRACT

Devices for assisting with the functioning of a tricuspid valve of a heart include a shaft, a flow optimizer, and an anchoring mechanism. A tilting mechanism can be configured to tilt the shaft relative to a central axis of the anchoring mechanism. Leaflets (e.g., multi-layer leaflets) of the flow optimizer can include a membrane and a rim, and the rim can have a higher stiffness than the membrane.

25 Claims, 22 Drawing Sheets

(56) References Cited

U.S. PATENT DOCUMENTS

| | | |
|---|---|---|
| 9,636,223 B2 | 5/2017 | Khalil et al. |
| 2002/0077696 A1 | 6/2002 | Zadno Azizi et al. |
| 2002/0095209 A1 | 7/2002 | Zadno Azizi et al. |
| 2005/0070999 A1 | 3/2005 | Spence |
| 2006/0178700 A1 | 8/2006 | Quinn |
| 2006/0241745 A1 | 10/2006 | Solem |
| 2007/0185571 A1 | 8/2007 | Kapadia et al. |
| 2007/0282429 A1 | 12/2007 | Hauser et al. |
| 2007/0293943 A1 | 12/2007 | Quinn |
| 2008/0033541 A1 | 2/2008 | Gelbart et al. |
| 2009/0222081 A1 | 9/2009 | Linder et al. |
| 2011/0077733 A1 | 3/2011 | Solem |
| 2014/0031928 A1 | 1/2014 | Murphy et al. |
| 2014/0067048 A1 | 3/2014 | Chau et al. |
| 2014/0114390 A1 | 4/2014 | Tobis et al. |
| 2015/0257885 A1 | 9/2015 | McGuckin |
| 2016/0030169 A1 | 2/2016 | Shahriari |
| 2016/0089238 A1 | 3/2016 | Centola et al. |
| 2016/0199181 A1 | 7/2016 | Kramer |
| 2016/0331523 A1* | 11/2016 | Chau .................... A61F 2/2463 |
| 2016/0367367 A1 | 12/2016 | Maisano et al. |
| 2017/0056176 A1 | 3/2017 | Rowe et al. |
| 2017/0079797 A1 | 3/2017 | Maisano et al. |
| 2017/0112618 A1 | 4/2017 | Li et al. |
| 2017/0239041 A1 | 8/2017 | Quinn |
| 2018/0168803 A1 | 6/2018 | Pesce |
| 2020/0113679 A1 | 4/2020 | Pesce et al. |

\* cited by examiner

500

Note: Arm 515a removed for clarity

Note: Cross-section

Note: Cross-section

Note: Cross-section

Note: Leaflets 550 removed for clarity

Note: Leaflets 550 removed for clarity

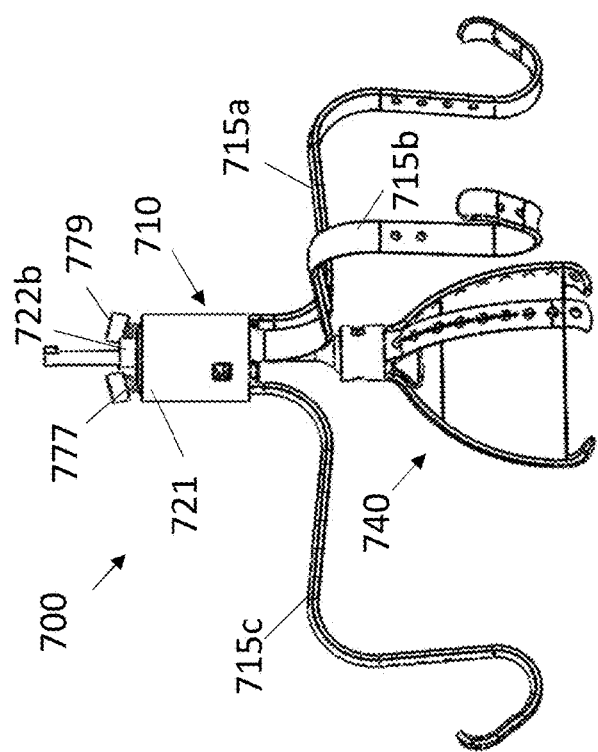
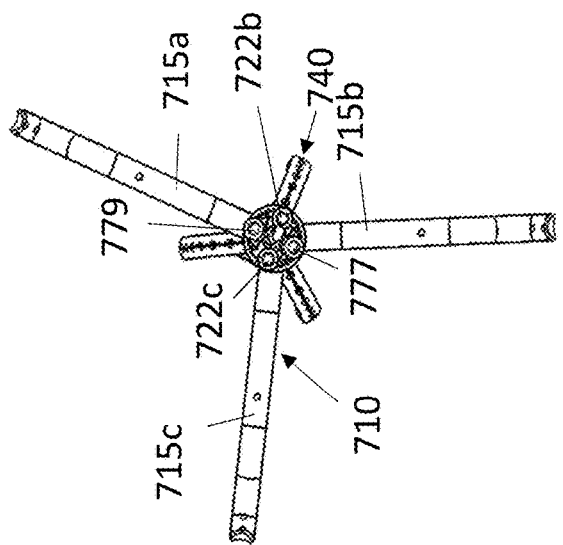

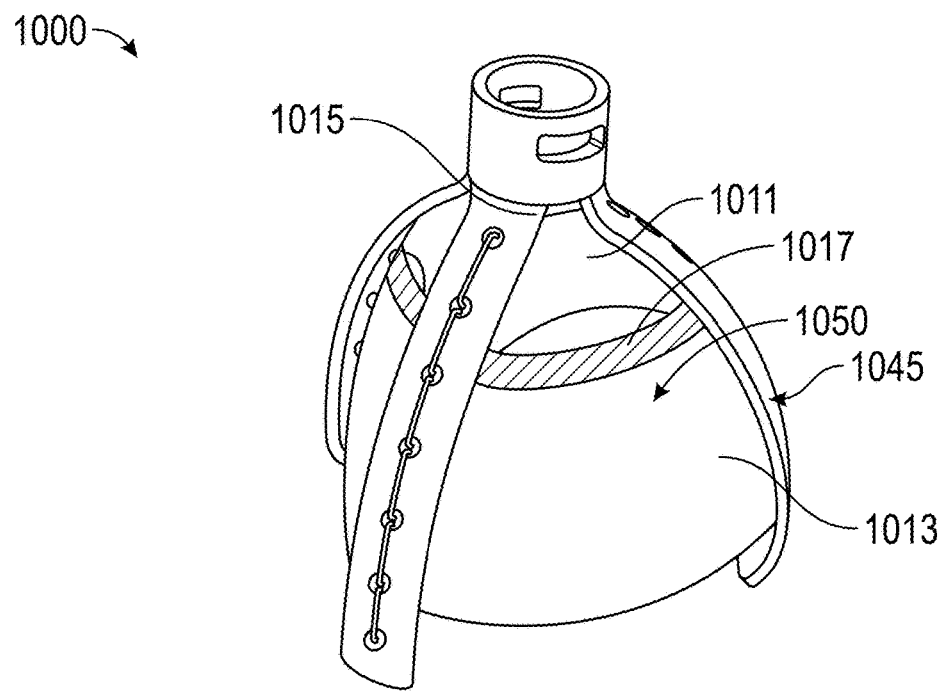
FIG. 11A
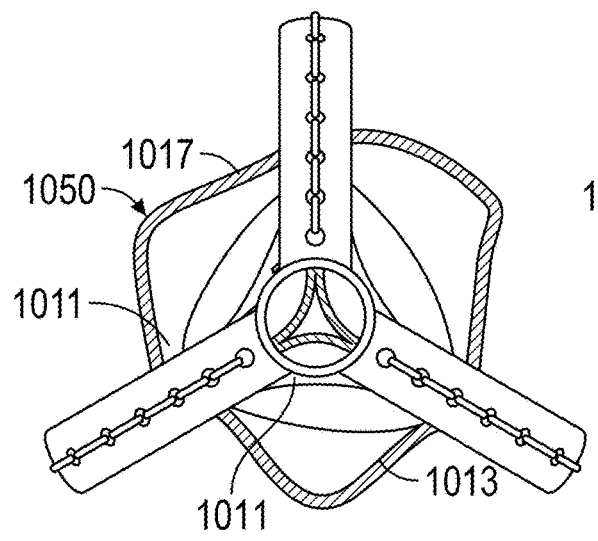  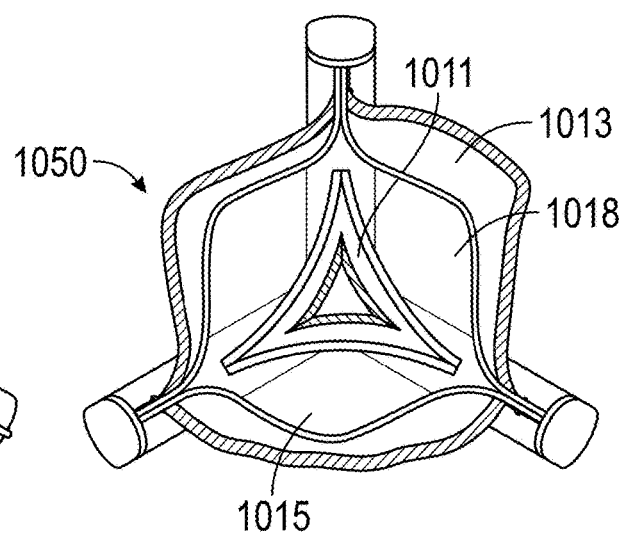
FIG. 11B     FIG. 11C

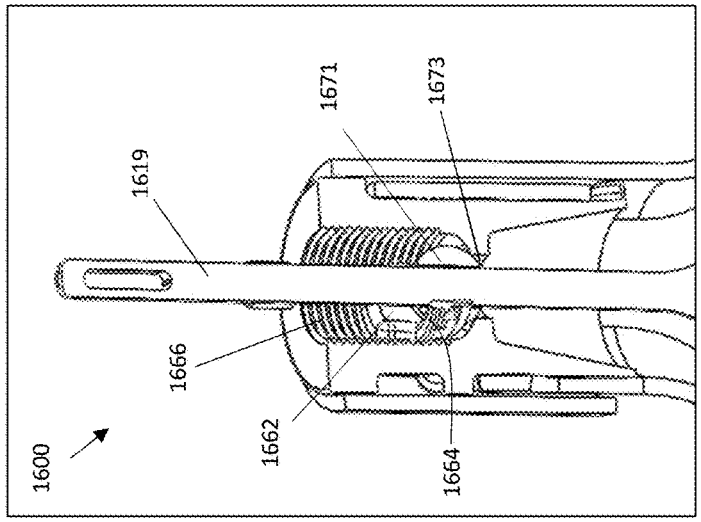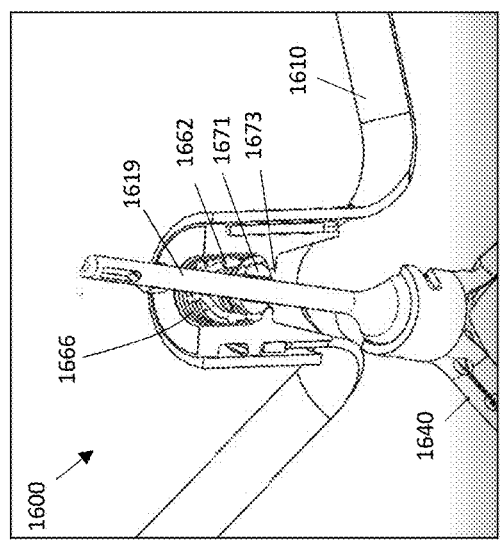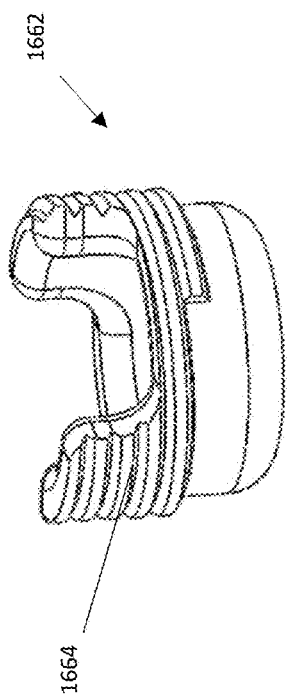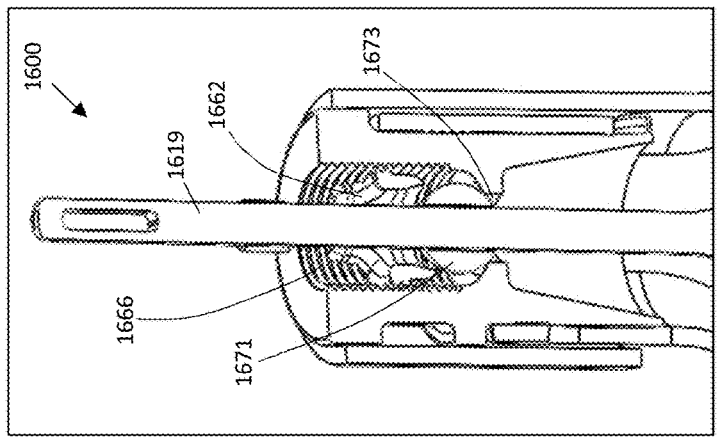
FIG. 16C
FIG. 16B
FIG. 16D
FIG. 16A

HEART VALVE SUPPORT DEVICE

CROSS REFERENCE TO RELATED APPLICATIONS

This application claims priority to U.S. Provisional Application No. 62/851,503, titled "Heart Valve Support Device," filed on May 22, 2019, and U.S. Provisional Application No. 62/976,232, titled "Heart Valve Support Device," filed on Feb. 13, 2020, the entireties of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

The tricuspid valve (TV) is an atrioventricular valve located in the right side of the human heart between the right atrium (RA) and the right ventricle (RV). The TV includes three asymmetrical leaflets (septal, anterior, and posterior) supported by a complex sub-valvular apparatus that includes the chordae tendineae and the papillary muscles. The TV is also in proximity to the tendon of Todaro, where the heart's delicate atrioventricular node is located.

Regurgitant flow occurs during the systolic phases of the cardiac cycle when the tricuspid valve becomes incompetent. The incompetence is often caused by the pathology-induced progressive enlargement of the valve's annulus, which prevents the leaflets from reaching full coaptation during systole (or during the systole phase of the cardiac cycle). The lack of coaptation can cause the development of a regurgitant orifice within the valve, through which blood can reenter the right atrium instead of exiting the right ventricle via the pulmonary valve. This condition can induce a cardiac overload with subsequent enlargement of the right ventricle and the right atrium, reduction of the right ventricular stroke volume, increase in systemic vein congestion, and other symptoms of congestive heart failure. Tricuspid valve regurgitation can be isolated from or associated with other valvulopathies and can lead to congestive heart failure, reduced functional cardiovascular capacity, and increased risks of untimely mortality.

Surgical repair or replacement are the most commonly used techniques for treating tricuspid valve regurgitation, but the clinical results (e.g. mortality and recurrence) are suboptimal. Moreover, due to the common presence of several comorbidities in patients affected by tricuspid regurgitation, the majority of patients are ineligible for surgical repair or replacement because of the high risk correlated with those procedures.

Transcatheter therapy does not require open-heart surgery and could be a viable and safer alternative. The unique anatomical features of the tricuspid valve, however, are a significant challenge for developing a safe and effective transcatheter implant. For example, anchoring the implant in the tricuspid valve may require burdening the adjacent cardiac structure (e.g. superior or inferior vena cava, the atrioventricular node, the coronary sinus, the right coronary artery, or the ventricular myocardium). Additionally, the low pressure and output of the hemodynamic flow at the tricuspid valve in the right side of the heart increases the risks of inducing atrioventricular pressure gradient and thrombogenesis. Accordingly, a transcatheter tricuspid valve implant that overcomes some or all of these challenges is desired.

SUMMARY OF THE DISCLOSURE

In general, in one embodiment, a device for assisting with functioning of a tricuspid valve of a heart includes a shaft, a flow optimizer, an anchoring mechanism, and a ball. The flow optimizer is fixedly connected to a distal end of the shaft. The anchoring mechanism includes a core with a socket therein. The ball is positioned within the socket and has a lumen therein through which the shaft is configured to extend. The ball is configured to rotate within the socket so as to tilt the shaft relative to a central axis of the anchoring mechanism.

In general, in one embodiment, a device for assisting with functioning of a tricuspid valve of a heart includes a shaft, a flow optimizer, an anchoring mechanism, and a rotation element. The flow optimizer is fixedly connected to a distal end region of the shaft. The anchoring mechanism includes a core with a socket therein. The rotation element is positioned within the socket and has a lumen therein through which the shaft is configured to extend. The rotation element is configured to rotate within the socket so as to tilt the shaft relative to a central axis of the anchoring mechanism.

This and other embodiments can include one or more of the following features. The shaft can be configured to slide axially and rotate within the lumen. The core can include an angled ledge configured to limit an angle of the flow optimizer relative to the anchoring mechanism. The angle can be less than 45 degrees. The device can further include a locking mechanism configured to lock an angle of tilt of the flow optimizer relative to the anchoring mechanism. The locking mechanism can be further configured to lock an axial and rotational position of the flow optimizer relative to the anchoring mechanism. The locking mechanism can include one or more screws configured to extend through the core and engage the ball. The locking mechanism can include an annular lock configured to fit between the core and the ball. The annular lock can be configured to move axially between a proximal position in which the ball is configured to rotate and a distal position in which the ball is fixed. The annular lock can be a snap fit lock. The annular lock can include threaded grooves configured to mate with threaded grooves on an inner surface of the core. The flow optimizer can include a frame and a plurality of leaflets attached to the frame. The plurality of leaflets can be configured to expand to an expanded configuration during systole to block a flow of blood around the flow optimizer and to collapse to a collapsed configuration during diastole to allow a flow of blood around the flow optimizer. The anchoring mechanism can further include a plurality of anchoring arms extending radially away from the core.

In general, in one embodiment, a method of assisting with functioning of a tricuspid valve of a heart includes: (1) inserting a tricuspid valve device into a native tricuspid valve, where the tricuspid valve devices includes a shaft, a flow optimizer, and an anchoring mechanism; (2) fixing the anchoring mechanism at commissures leaflets of the native tricuspid valve; and (3) tilting the shaft relative to a central axis of the anchoring mechanism so as to position the flow optimizer at a desired angular positon within the native tricuspid valve.

This and other embodiments can include one or more of the following features. Tilting the shaft can include rotating a ball within a socket of the tricuspid valve device. The method can further include, during diastole, reducing a cross-sectional area of the flow optimizer to allow hemodynamic flow around and through the flow optimizer, and during systole, increasing a cross-sectional area of the flow optimizer to seal an orifice of the native tricuspid valve. The method can further include axially moving the shaft relative to the anchoring mechanism after fixing the anchoring mechanism so as to position the flow optimizer at a desired axial position within the native tricuspid valve. The method can further include rotating the shaft relative to the anchoring mechanism after fixing the anchoring mechanism so as to position the flow optimizer at a desired rotational position within the native tricuspid valve. The method can further include locking the flow optimizer at the desired angular position with a locking mechanism. The locking mechanism can further lock an axial and rotational position of the flow optimizer relative to the anchoring mechanism. The locking mechanism can include one or more screws configured to extend through the core and engage with the ball. The locking mechanism can include an annular lock configured to fit around the shaft. Locking can include distally moving the annular lock relative to the anchoring mechanism. Locking can include rotating the annular lock relative to the anchoring mechanism.

In general, in one embodiment, a device for assisting with functioning of a tricuspid valve of a heart includes a flow optimizer that includes a frame having a plurality of arms and a plurality of leaflets attached to the plurality of arms. The plurality of leaflets are configured to expand to an expanded configuration during systole to block a flow of blood around the flow optimizer and to collapse to a collapsed configuration during diastole to allow a flow of blood around the flow optimizer. Each of the leaflets of the plurality of leaflets includes a membrane and a rim, and the rim has a higher stiffness than the membrane.

This and other embodiments can include one or more of the following features. The plurality of leaflets can be further configured to collapse to the collapsed configuration to allow a flow of blood through the flow optimizer. The membrane can have a thickness that is less than 75% of a thickness of the rim. Each of the plurality of leaflets can have a substantially triangular shape. Each of the plurality of leaflets can include a first layer and a second layer, and the second layer can at least partially overlap the first layer. The first layer can be configured to be positioned towards an atrium, and the second layer can be configured to be positioned towards a ventricle. The second layer can be positioned radially outwards of the first layer such that a gap is formed between an atrial end of the second layer and a ventricular end of the first layer. The second layer can be substantially quadrilateral in shape, and the first layer can be substantially triangular in shape. The rim can be positioned along two edges and not along the ventricular end of the first layer. The rim can be positioned along three edges and not along a ventricular end of the second layer. The leaflets can have first, second, and third edges, and the rim can be positioned along only the first and second edges. The first and second edges can meet at an apex configured to be positioned closer to an atrium than the third edge. The plurality of leaflets can be sewn to the frame with a plurality of stitches that extend parallel to the arms of the frame. The rim can include a fabric. The fabric can be polyethylene terephthalate. The fabric can be coated with polyurethane and silicone. The membrane can include a polymer membrane. The membrane can include polyurethane and silicone. The device can further include an anchoring mechanism configured to anchor the device in a native tricuspid valve. The anchoring mechanism can include a plurality of anchoring arms extending radially therefrom.

In general, in one embodiment, a method of assisting with functioning of a tricuspid valve of a heart includes: (1) implanting a flow optimizer into a native tricuspid valve orifice, where the flow optimizer includes a plurality of leaflets, and where each leaflet has a first layer and a second layer, the first and second layers each including a membrane and a rim; (2) during diastole, collapsing the plurality of leaflets to allow hemodynamic flow around and through the flow optimizer, where collapsing the plurality of leaflets includes moving the first layer radially inwards before a second layer so as to create a gap therebetween; and (3) during systole, expanding the plurality of leaflets to seal the tricuspid valve orifice.

This and other embodiments can include one or more of the following features. The rim can have a higher stiffness than the membrane. The second layer can at least partially overlap the first layer. The first layer can be positioned towards an atrium, and the second layer can be positioned towards a ventricle. The second layer can be positioned radially outwards of the first layer such that the gap is formed between an atrial end of the second layer and a ventricular end of the first layer. The second layer can be substantially quadrilateral in shape, and the first layer can be substantially triangular in shape. The rim can be positioned along two edges and not along the ventricular end of the first layer. The rim can be positioned along three edges and not along a ventricular end of the second layer. Expanding the plurality of leaflets can include closing the gap.

In general, in one embodiment, an apparatus for implantation includes a shaft, a flow optimizer fixedly connected to the shaft, and an anchoring mechanism. The shaft is configured to slide axially and rotationally relative to the anchoring mechanism so as to adjust the axial and rotational position of the flow optimizer relative to the anchoring mechanism.

This and other embodiments can include one or more of the following features. The apparatus can further include a locking mechanism configured to lock an axial and rotational position of the anchoring mechanism relative to the flow optimizer. The locking mechanism can include one or more screws configured to extend through the core and engage with the shaft.

In general, in one embodiment, a device for assisting with functioning of a tricuspid valve of a heart includes a shaft, a flow optimizer fixedly connected the distal end region of the shaft, and an anchoring mechanism connected to the proximal end region of the shaft. The anchoring mechanism includes a core and a plurality of arms extending radially therefrom. A first arm of the plurality of arms is fixedly attached to the core, and a second arm of the plurality of arms is rotationally attached to the core. The second arm is configured to move along a cam surface to set an angular placement of the second arm relative to the first arm.

This and other embodiments can include one or more of the following features. The device can further include a locking mechanism configured to lock the angular placement of the second arm relative to the first arm. The locking mechanism can include one or more screws.

This and other embodiments can include one or more of the following features. Each of the arms can be configured to be placed at a commissure of the tricuspid valve. The plurality of arms can further include a third arm, and the third arm can be configured to move along a cam surface to set an angular placement of the third arm relative to the first arm and the second arm.

In general, in one embodiment, an apparatus for implantation includes a shaft, a flow optimizer fixedly connected to the shaft, and an anchoring mechanism. The anchoring mechanism includes a plurality of arms that include a curved elongate element and a covering positioned over a distal end of the elongate element.

This and other embodiments can include one or more of the following features. The covering can include polyethylene terephthalate. The covering can extend around only an outer 10-40% of the arm. The arm can include a metal. The covering can include a cushion and a sleeve. The cushion can include 3-10 layers of fabric. Each of the arms can be configured to be placed at a commissure of the tricuspid valve.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 7A is a side perspective view of another valve support device.

FIG. 7B is a top view of the valve support device of FIG. 7A.

FIG. 11A is a perspective view of the flow optimizer of FIG. 10A with the top layer collapsed and the bottom layer expanded.

FIG. 11B is a top view of the flow optimizer of FIG. 11A.

FIG. 11C is a bottom view of the flow optimizer of FIG. 11A.

FIG. 16A is a cross-sectional view of the proximal end of a valve support device with an annular lock in a proximal (unlocked) configuration.

FIG. 16B is a perspective view of the valve support device of FIG. 16A with the annular lock in the proximal position and the flow optimizer tilted relative to the anchoring mechanism.

FIG. 16C is a cross-sectional view of the valve support device of FIG. 16A with the annular lock in the distal (locked) configuration.

FIG. 16D is a perspective view of the annular lock of the device of FIG. 16A.

DETAILED DESCRIPTION

Described herein are catheter-delivered intracardiac implants for supporting and improving the function of the tricuspid valve. The tricuspid valve implants (also called tricuspid valve support devices) can include a flow optimizer and/or an anchor, either or both of which can be configured to accommodate the anatomically and hemodynamically challenging location within the tricuspid valve. The flow optimizer, for example, can be configured such that, during the diastolic phase of the cardiac cycle, it minimizes its cross-sectional area and allows hemodynamic flow around and through the implant, thus minimizing the potential risk of inducing atrioventricular pressure gradient and thrombogenesis. During the systolic phase, the flow optimizer can expand to seal or minimize the regurgitant orifice and reinstate the efficacy of the tricuspid valve. Further, the anchor, for example, can be configured to anchor the implant proximate to the tricuspid valve without requiring traumatic interaction with the tricuspid valve, right atrium, or right ventricle. The implant can permit intra-procedural adjustments under standard imaging techniques (e.g. fluoroscopy, echocardiography) of the position of the flow optimizer within the native tricuspid valve, thereby providing for real-time optimization of the hemodynamic flow across the tricuspid valve. The implant described herein can advantageously increase the efficacy, safety, and procedural success of transcatheter therapy of tricuspid valve regurgitation.

The flow optimizer can be placed within the lumen of the tricuspid valve and can permit diastolic hemodynamic flow from the right atrium into the right ventricle and, during systole, reduce or prevent blood regurgitation from the right ventricle into the right atrium. The flow optimizer can be placed within the tricuspid valve on the ventricular (distal or bottom) side. The anchor, to which the flow optimizer can be directly connected, can engage the tricuspid valve annulus at the commissures of the native leaflets. Anchoring can be achieved from the atrial (proximal or top) side. In some embodiments, the device can be anchored within the right atrium at the commissures. When implanted at the tricuspid valve, the device can seal the coaptation gap between the native leaflets during the systolic phase of the cardiac cycle and allow blood flow from the right atrium to the right ventricle during the diastolic phase of the cardiac cycle.

The tricuspid valve support devices described herein can be used to reduce or prevent tricuspid regurgitation. The devices can be configured to adopt a crimped conformation so as to be deployed using a standard intravascular catheter. Further, the devices can be configured to adopt a deployed conformation upon placement within the body.

Although shown and described with reference to a tricuspid valve, the device, the flow optimizer and/or the anchoring mechanism can be adapted for use in any valve of the heart.

Figure 1A:
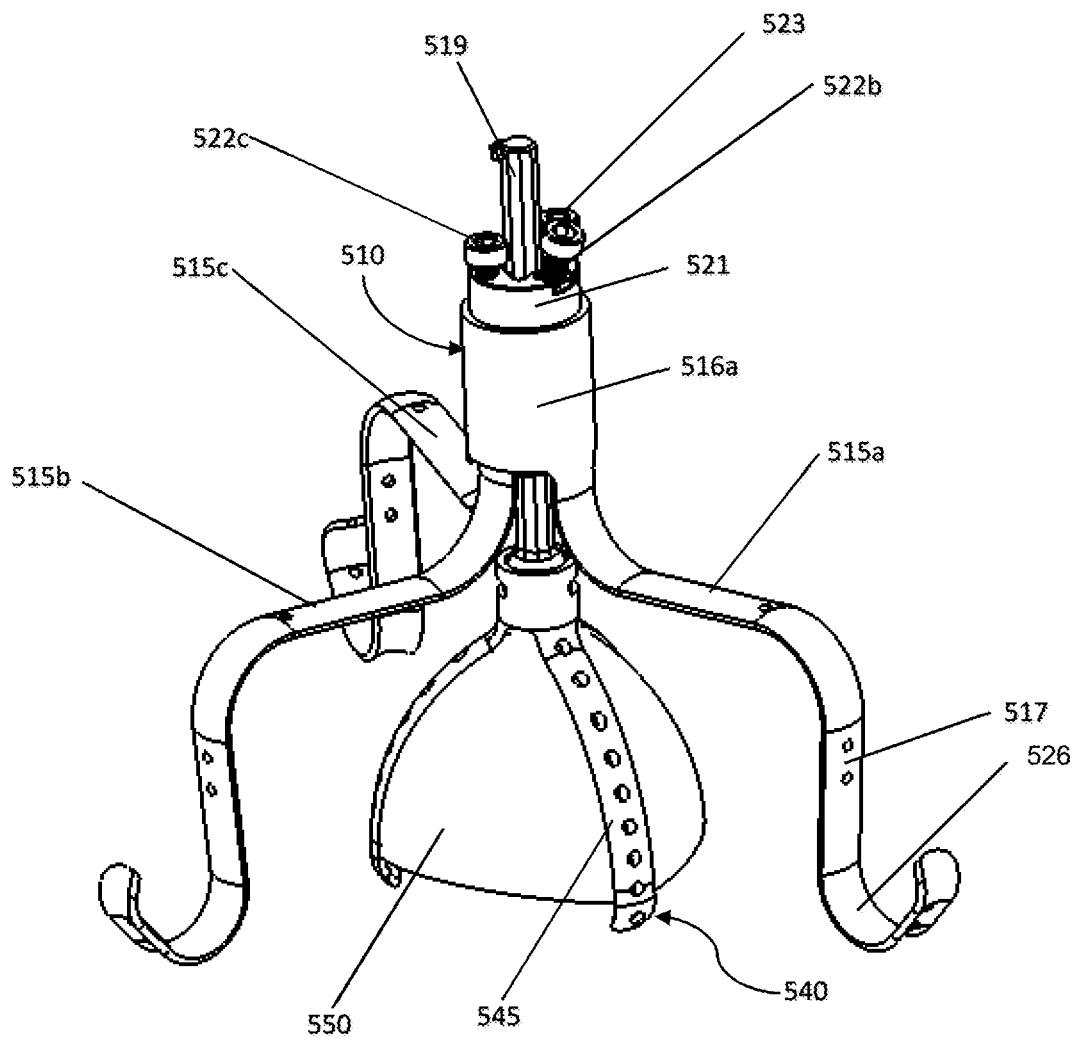
FIG. 1A is a side perspective view of a valve support device.
Figure 1B:
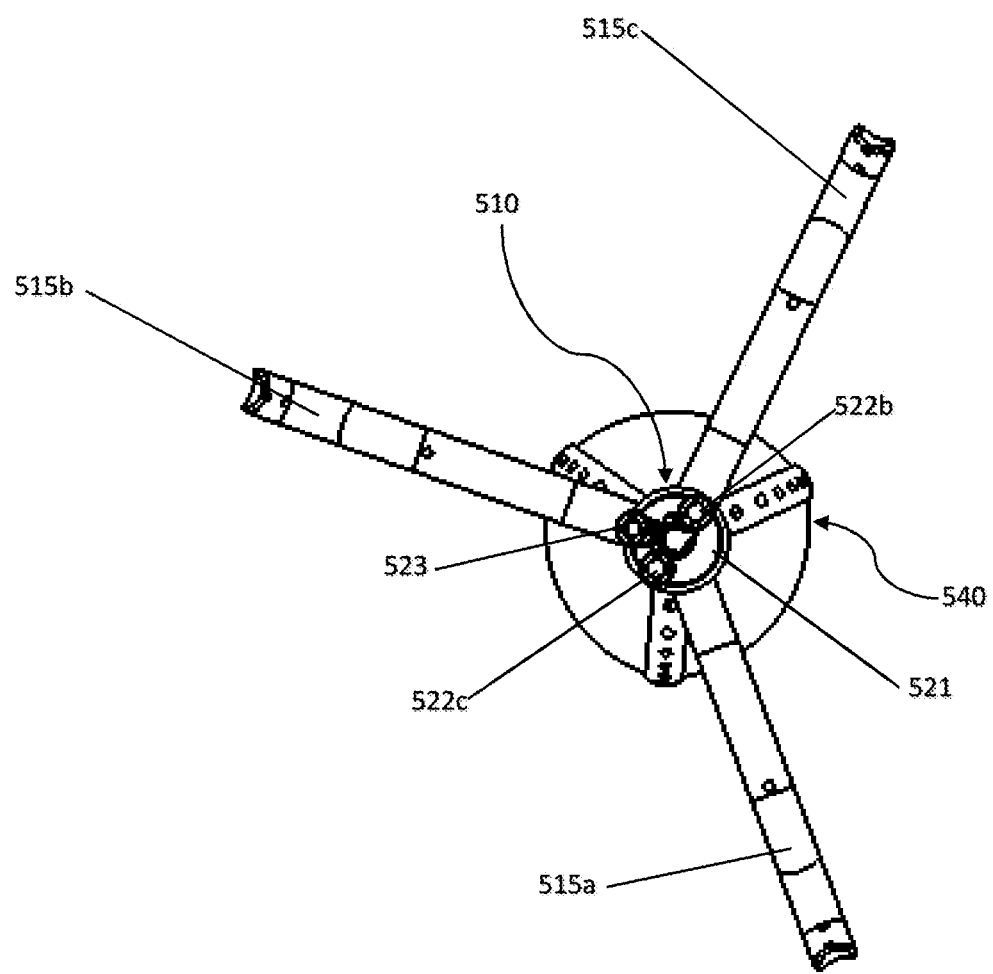
FIG. 1B is a top view of the valve support device of FIG. 1A.

FIGS. 1A-1B illustrate a tricuspid valve support device 500 in a deployed configuration (and with leaflets expanded). The device 500 is configured to be anchored at the annulus of the tricuspid valve. The device 500 includes an anchoring mechanism 510 and a flow optimizer 540 connected with a shaft 519.

Figure 2:
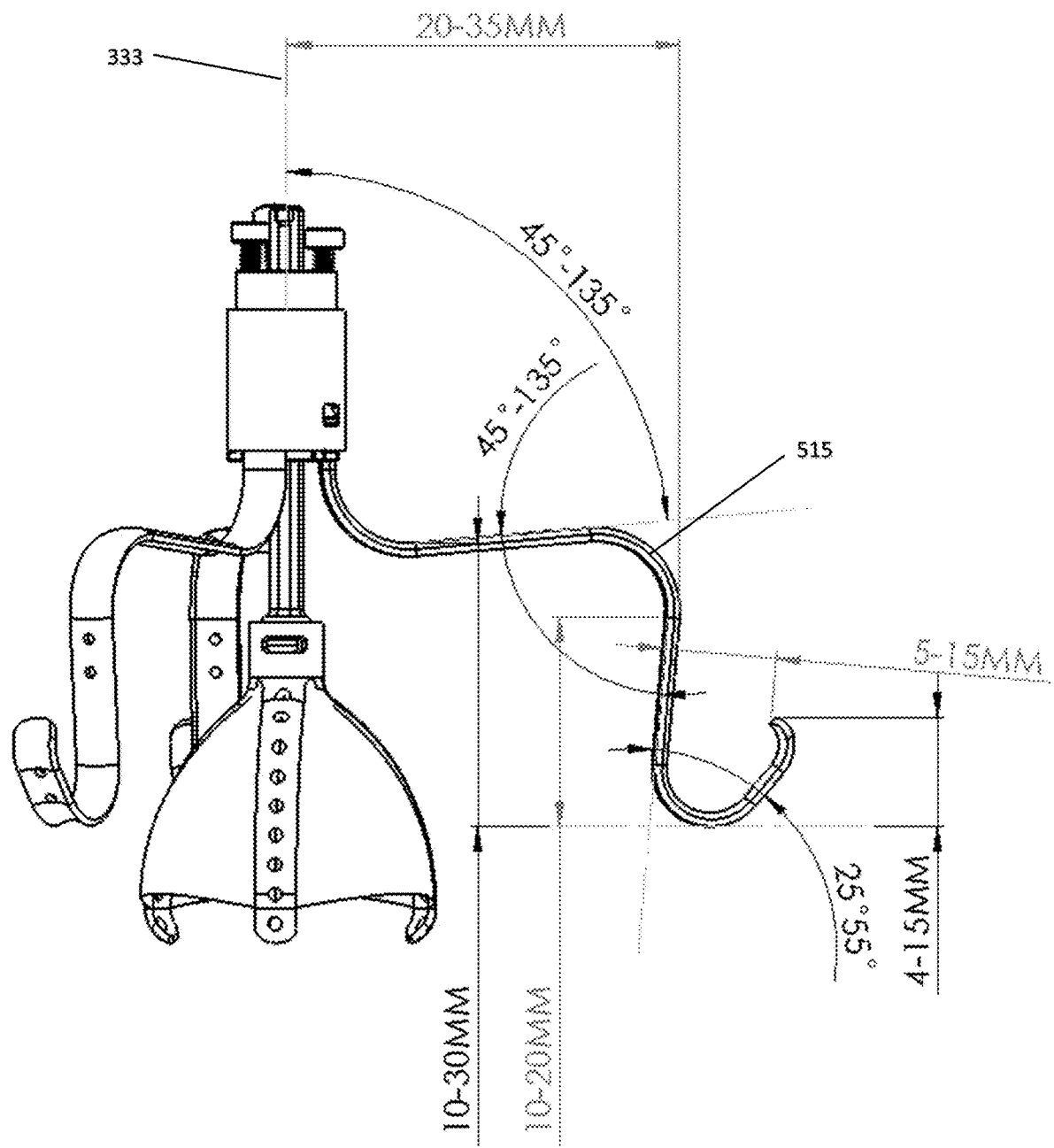
FIG. 2 is a side view of a valve support device showing exemplary dimensions.
Figure 3:
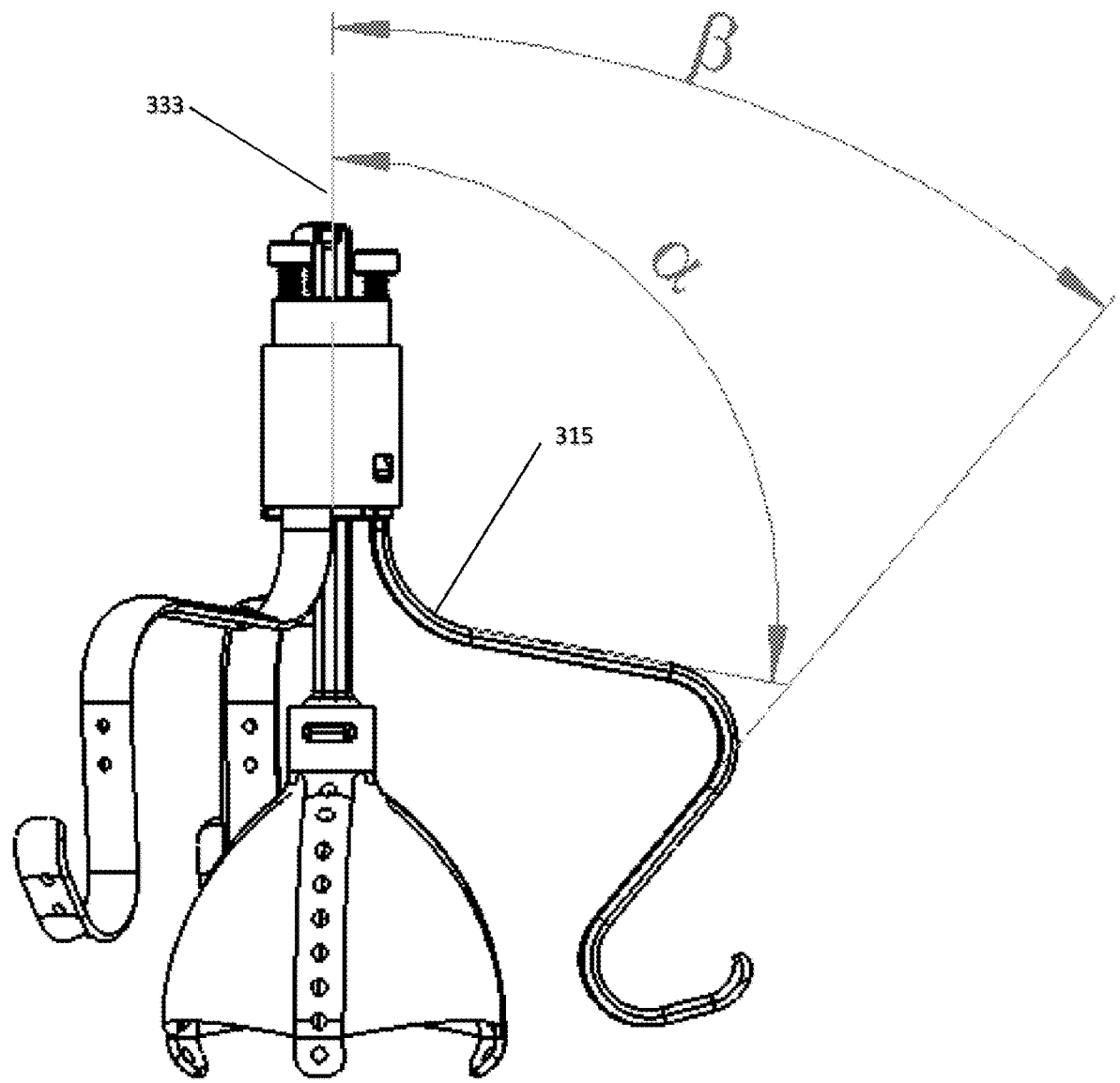
FIG. 3 is a side view of a valve support device with exemplary defined angles.

The anchoring mechanism 510 include a plurality of arms 515*a-c* that are radially disposed around and from an inner core 521 of the device 500. The end region (or distal end region) 526 of the arms 515*a*-515*c* can be contoured to mate with the tissue wall of the tricuspid valve annulus at the commissures of the native leaflets. The intermediate portion 517 of the arms 515*a-c* can be shaped to conform to the inner supra-annular wall of the right atrium to provide further support and/or stabilization. The arms 515*a-c* can be made, for example, of a shape memory material, such as nitinol, so as to collapse for delivery and self-expand outward to conform to the anatomy of the tricuspid valve. When deployed in the tricuspid valve, the end regions 526 of the arms 515*a*-515*c* can mate with the tissue wall of the tricuspid valve annulus at the commissures of the leaflets, and the intermediate portion 517 can rest against the inner supra-annular wall of the right atrium to provide further retention and stabilization to the tricuspid valve flow optimizer 540. Exemplary dimensions and angles of an arm 515 (which can be any of arms 515*a-c*) are shown in FIG. 2. The specific shape of the arms 515*a-c* is exemplary, and it should be understood that other shapes, and corresponding dimensions and angles, are possible. For example, FIG. 3 shows an arm 315 that extends at a wider angle α and angle β relative to the longitudinal axis 333 of the device than the arm 515.

Figure 4A:
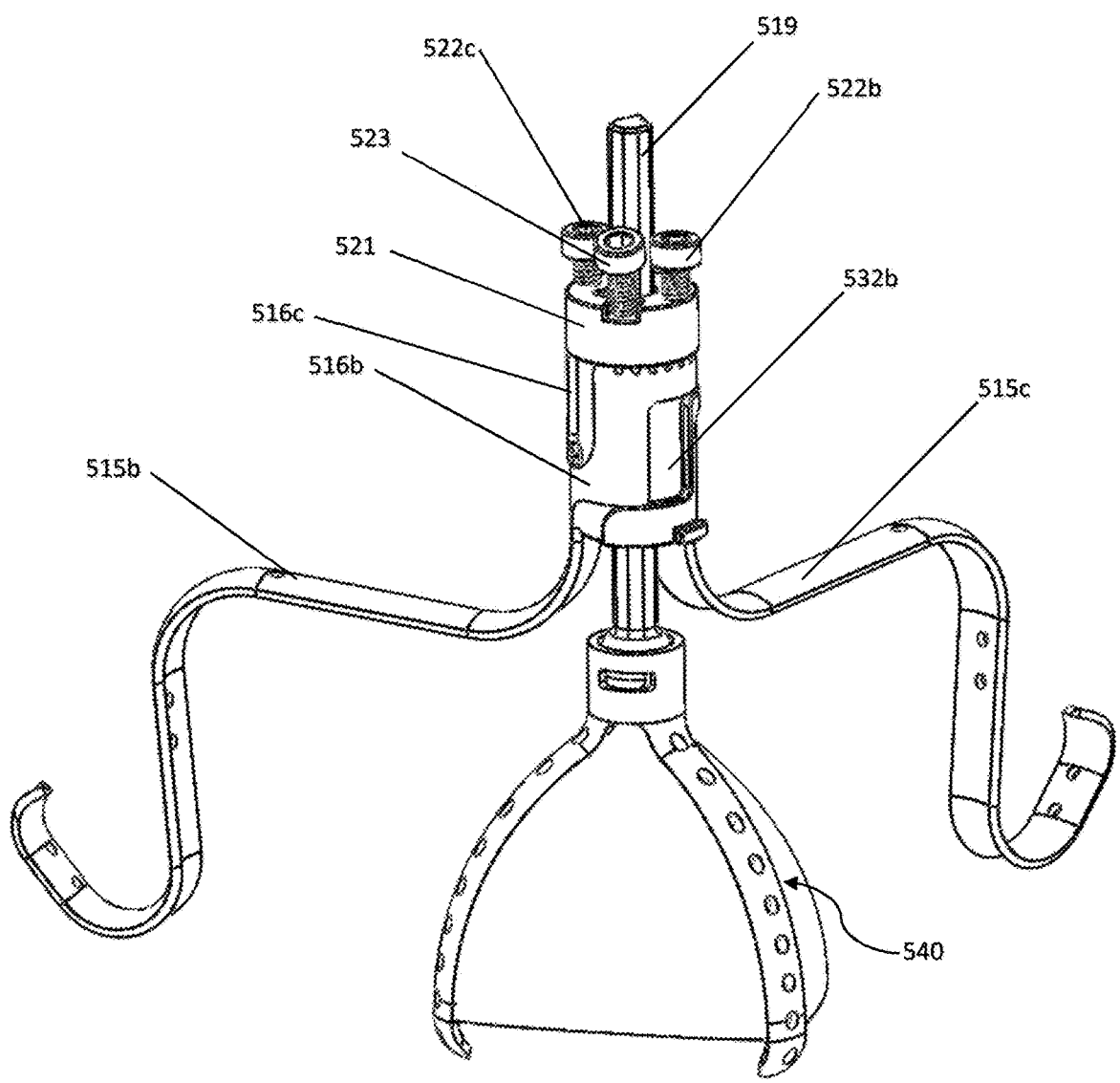
FIG. 4A is a perspective view of the valve support device of FIGS. 1A-1B with one anchoring arm removed for clarity.
Figure 4B:
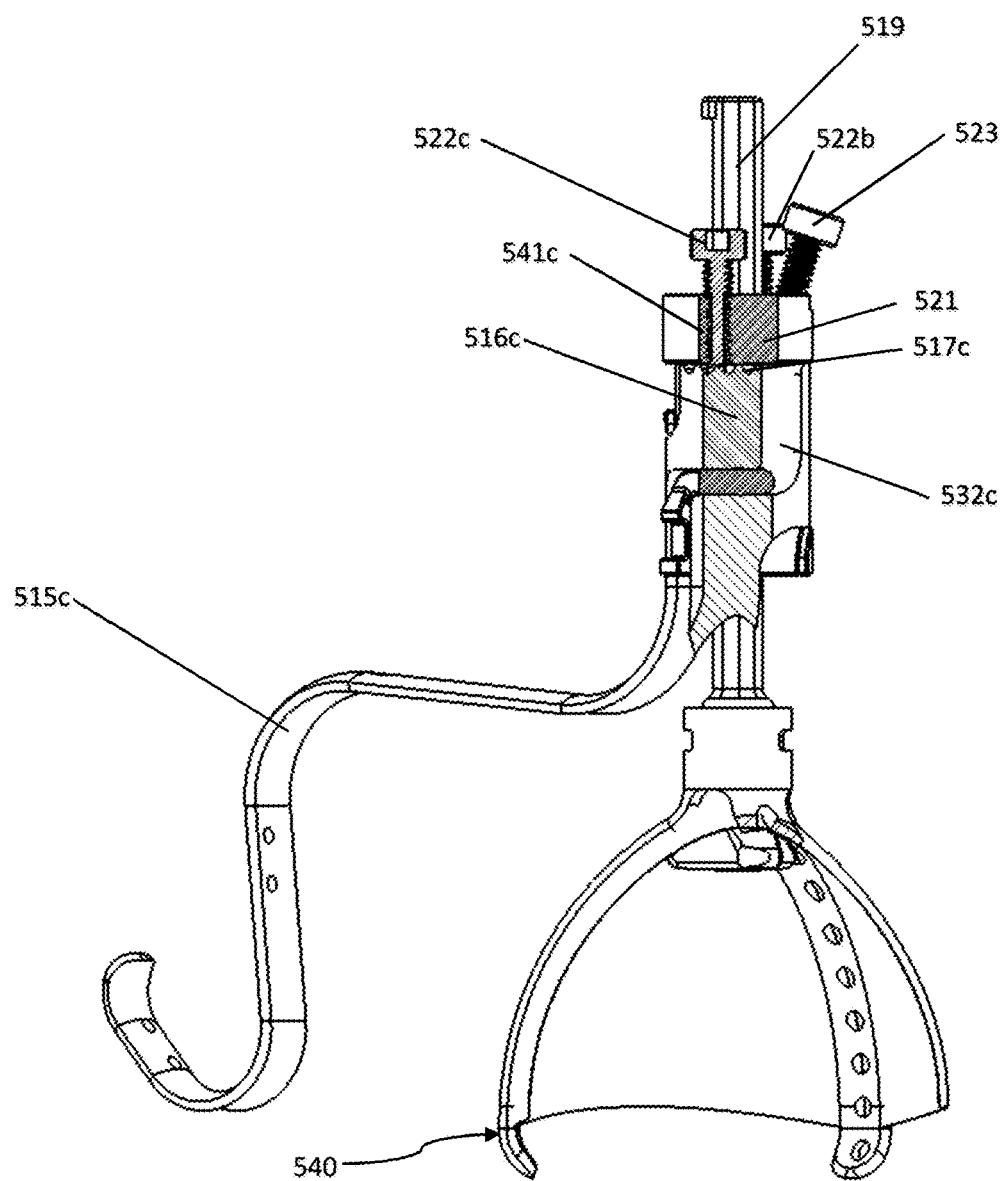
FIG. 4B is a cross-sectional view of the valve support device of FIGS. 1A-1B.
Figure 4C:
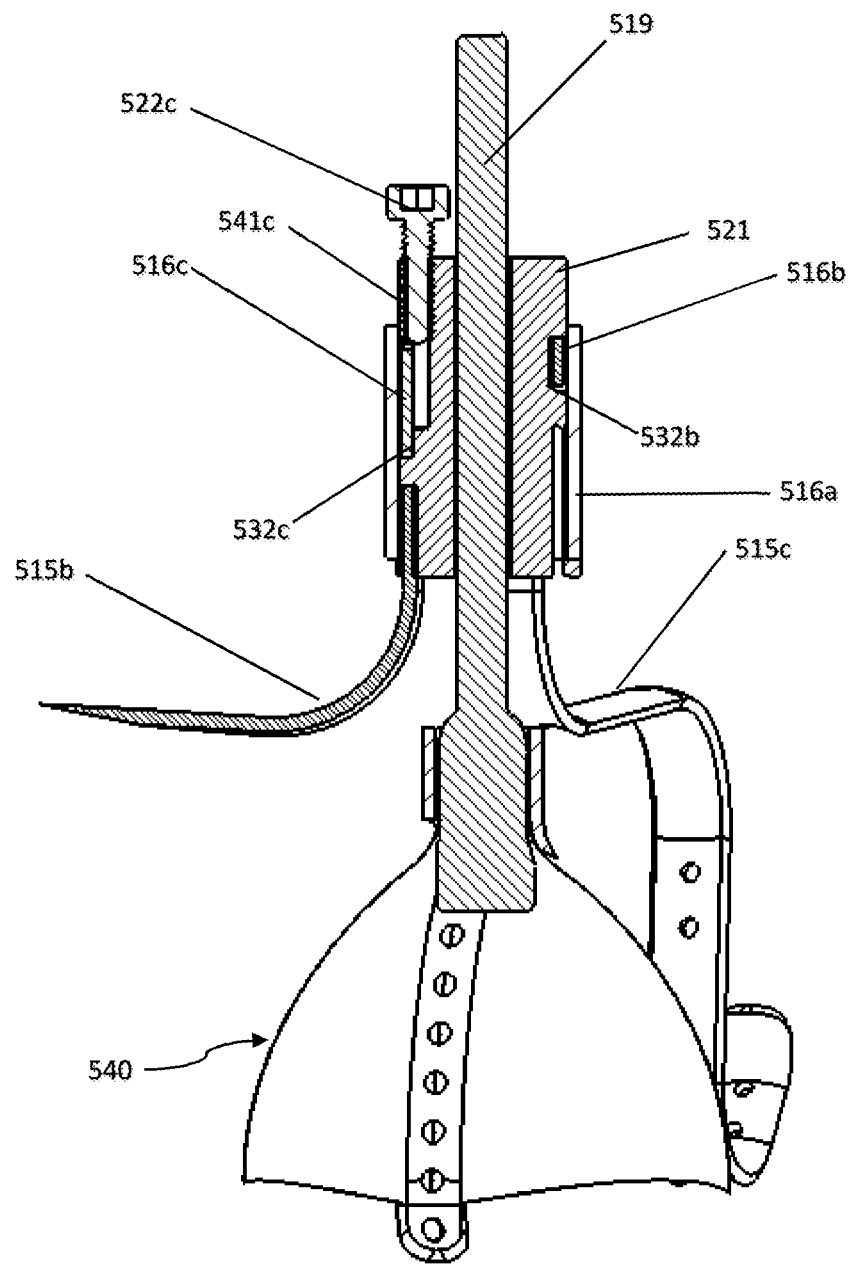
FIG. 4C is another cross-sectional view of the valve support device of FIGS. 1A-1B.

Referring to FIGS. 4A-4C, one or more of the arms 515*a-c* of the anchoring assembly 510 of device 500 can be configured to rotate about the inner core 521. In one embodiment, one arm (515*a*) can remain fixed relative to the inner core 521 while the other two arms (515*b*, 515*c*) can independently rotate clockwise or counterclockwise relative to the inner core 521. For example, fixed arm 515*a* can have a cylindrical proximal portion 516*a*, which can be fixed to the inner core 521, for example, via a snap fit mechanism. The second arm 515*b* can have a proximal portion 516*b* that slides circumferentially along a cam surface 532*b* on the inner core 521. Similarly, the third arm 515*c* can have a proximal portion 516*c* that slides circumferentially along a second cam surface 532*c* on the inner core 521. Once the arms 515*b,c* have reached their desired circumferential position, the arms 515*b,c* can be individually locked in place via activation of the screws 522*b*, 522*c*. For example, screw 522*c* can be configured to extend through a threaded hole 541*c* in the inner core 521. When the screw 522 extends distally out of the hole 541*c*, it can engage with the undulated proximal edge 517*c* of proximal portion 516*c*. In some embodiments, engagement with this undulated edge 517*c* can prevent the arm 515*c* from moving. In other embodiments, the screw 522*c* can extend between the inner core 521 and the proximal portion 516*c* to force the proximal portion 516*c* against the cylindrical proximal portion 516*a* of fixed arm 515*a*, thereby preventing the arm 515*c* from moving due to friction. The screw 522*b* can similarly lock the arm 515*b* in place.

By rotating the arms 515*b*, 515*c*, an operator can advantageously individually position arms 515*b*-515*c* at different relative angles relative to the arm 515*a*, thereby matching angles across the commissures of the leaflets of the patients' native tricuspid valves. The rotation and locking of the arms 515*b-c* can be performed pre-procedurally (for example, prior to loading of the device 500 into the delivery catheter), and/or intra-procedurally.

Figure 5A:
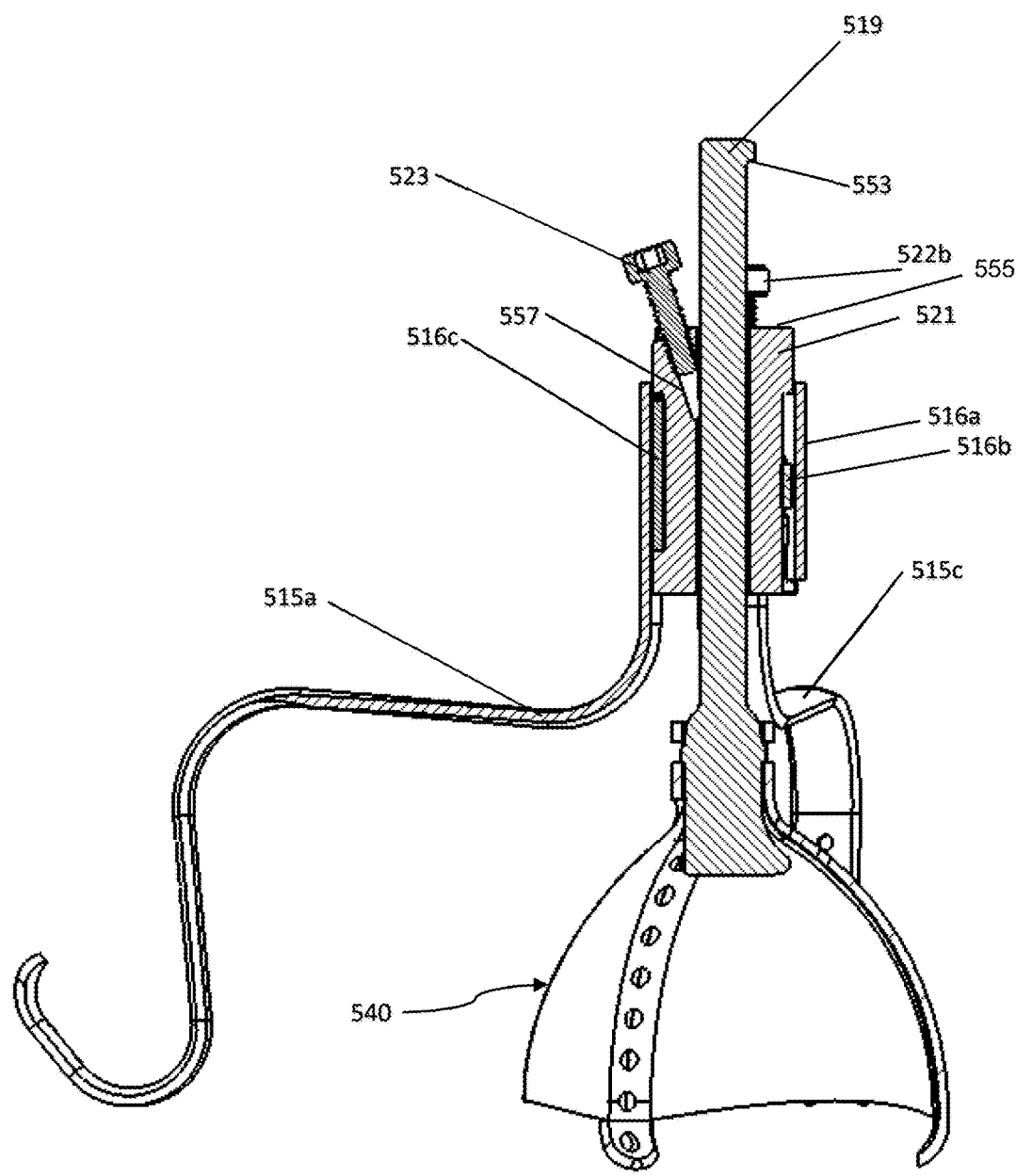
FIG. 5A is another cross-sectional view of the valve support device of FIGS. 1A-1B.
Figure 5B:
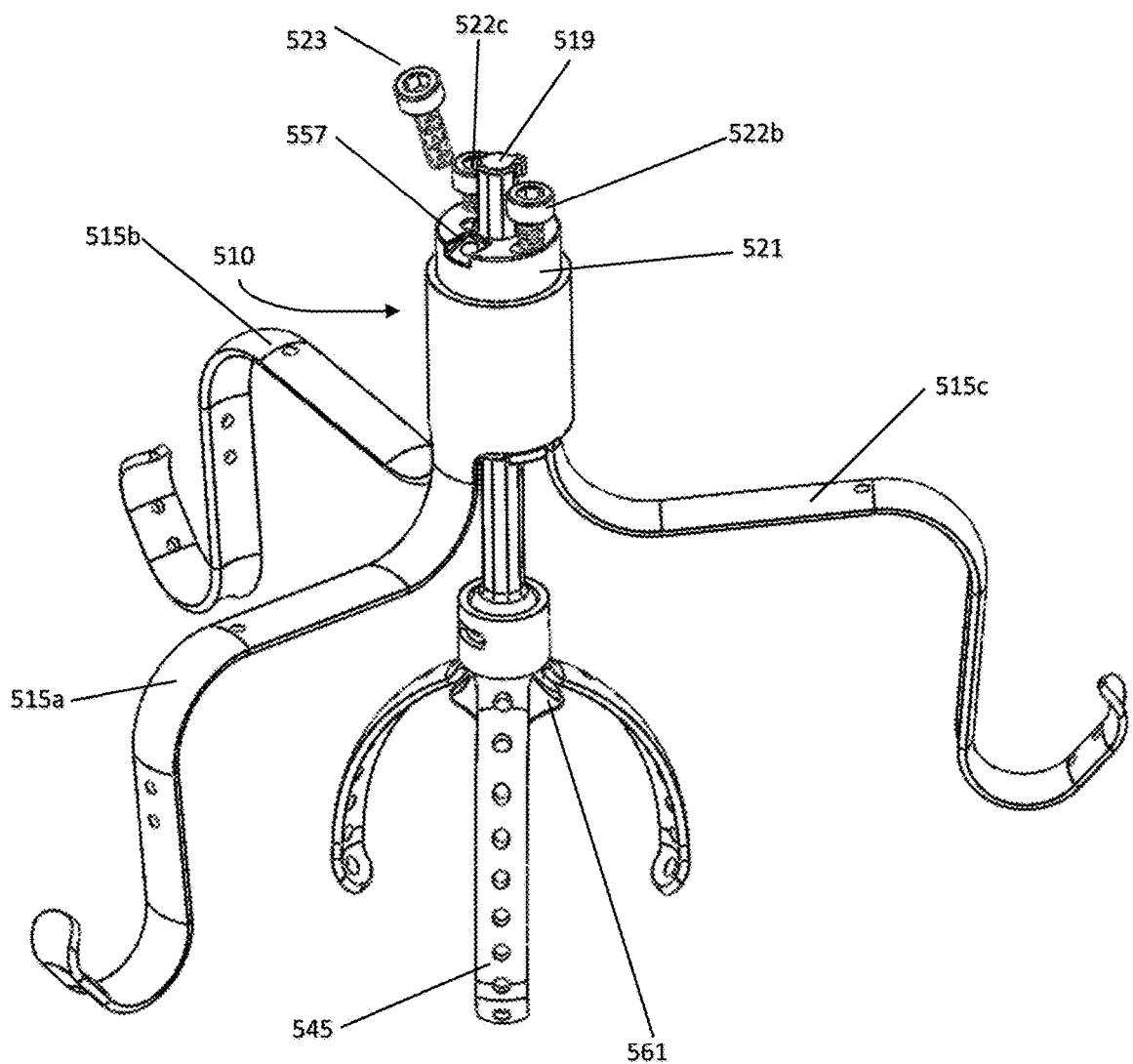
FIG. 5B is a perspective view of the valve support device of FIGS. 1A-1B without the leaflets for clarity.

Referring to FIGS. 5A-5B, the shaft 519, which is fixed to the flow optimizer 540, can be configured to slide and/or rotate axially relative to the anchoring mechanism 510 to provide for axial and rotational adjustment of the relative positions of the anchoring mechanism 510 and the flow optimizer 540 in device 500. For example, the shaft 519 can slide or rotate within a central lumen 551 of the inner core 521. A lip 553 on the proximal end of the shaft 519 can be configured to butt against the proximal end 555 of the inner core 521 to prevent the flow optimizer 540 from completely disengaging with the anchoring assembly 510. Further, once the flow optimizer 540 and anchoring assembly 510 are at the desired relative positions, the flow optimizer 540 and anchoring assembly 510 can be locked in position relative to one another via activation of the screw 523. The screw 523 can engage with (and rotate within) a threaded hole 557 in the inner core 521. The threaded hole 557 can extend at an angle relative to the longitudinal axis of the device (e.g., at an angle of 30-45 degrees). As the screw 523 is moved into engagement with the shaft 519, it can push the shaft 519 against the inner core 521, thereby preventing movement of the shaft 519 relative to the inner core 521 via friction.

The axial and rotational positioning of the flow optimizer 540 relative to the anchoring assembly 510 can be performed pre-procedurally (for example, prior to loading of the device 400 into the delivery catheter), and/or intra-procedurally. Advantageously, when performed while the device 500 is in place in the body, the axial position can be set without requiring rotation of the flow optimizer 540, thereby reducing unwanted interaction with, and/or catching on, the native anatomy. Further, the rotational position of the flow optimizer 540 relative to the anchoring assembly 510 can advantageously be specifically set by rotating the shaft 510 (e.g., once the device 500 is in place in the body), thereby allowing precise positioning of the flow optimizer 540 relative to the native tricuspid valve and optimization of its position relative to the regurgitant orifice.

Figure 6:
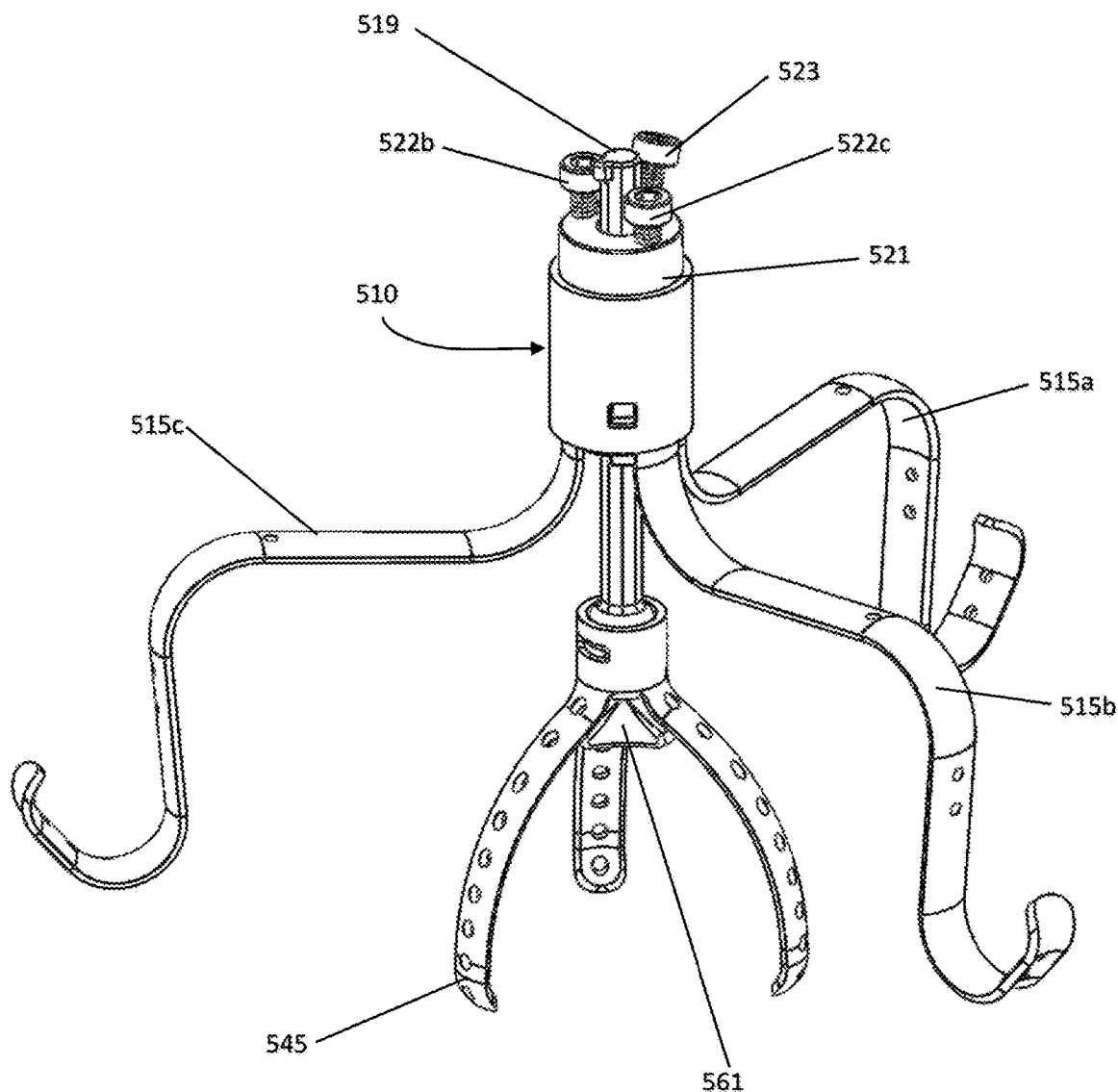
FIG. 6 is another perspective view of the valve support device of FIGS. 1A-1B without the leaflets for clarity.
Figure 7C:
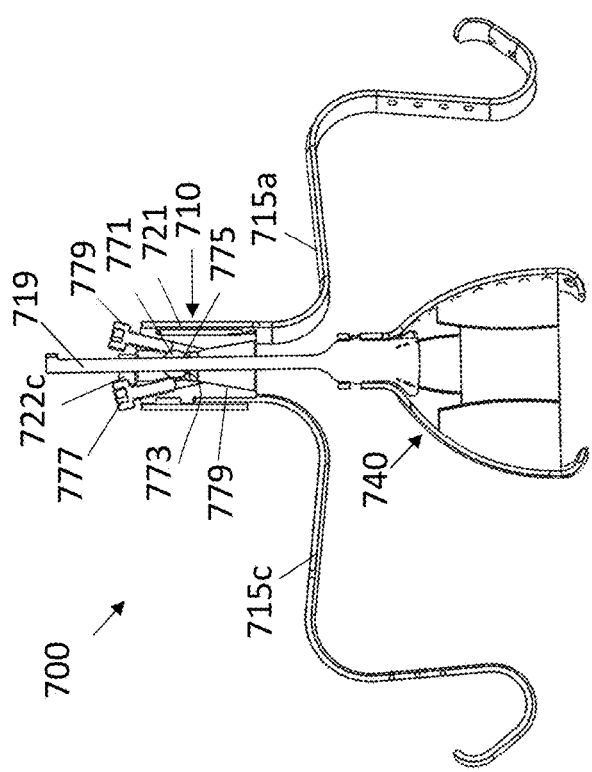
FIG. 7C is a cross-sectional view of the valve support device of FIG. 7A.
Figure 8A:
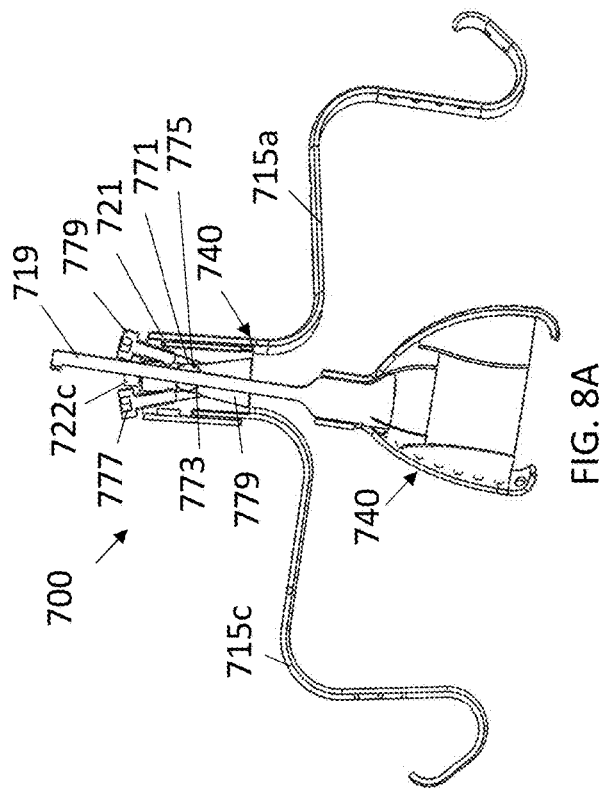
FIG. 8A is a cross-sectional view of the valve support device of FIG. 7A with the flow optimizer tilted relative to the anchoring assembly.
Figure 8B:
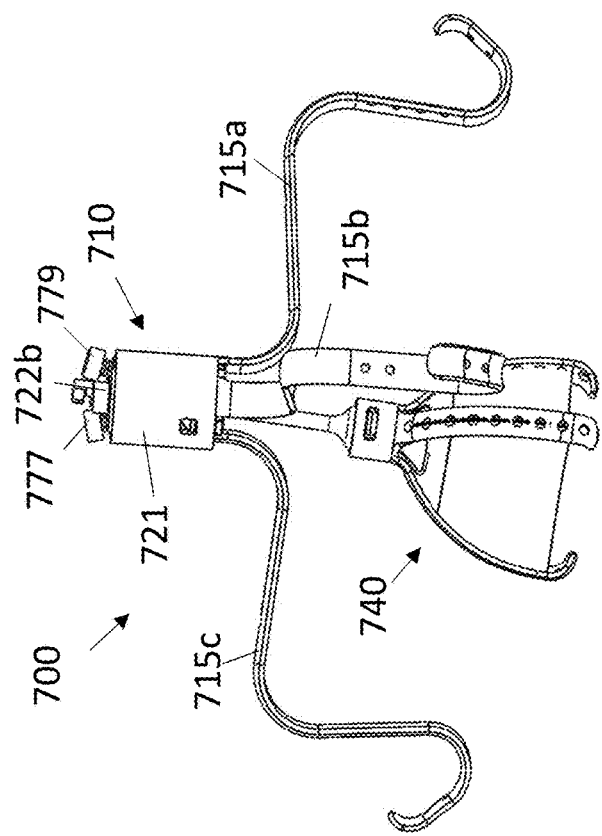
FIG. 8B is a side perspective view of the valve support device of FIG. 8A
Figure 8C:
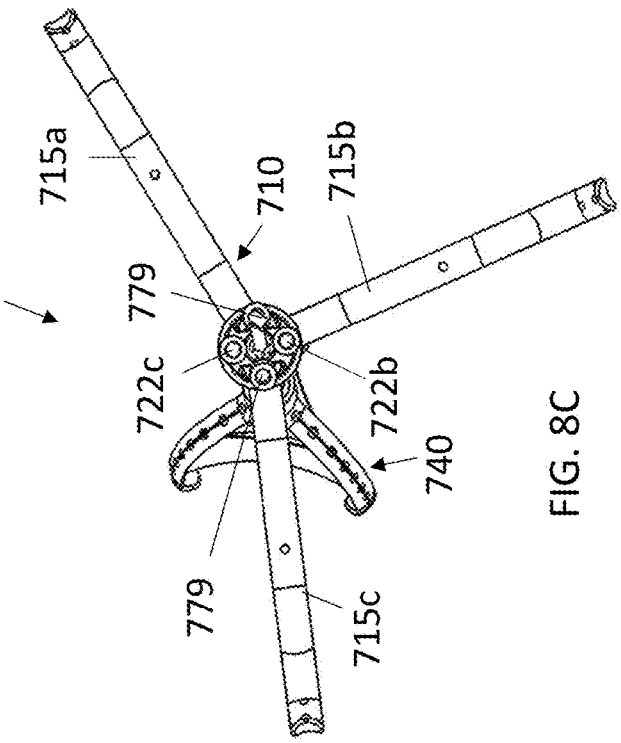
FIG. 8C is a top perspective view of the valve support device of FIG. 8A.

Referring back to FIG. 1A, the flow optimizer 540 can include a frame 545 supporting leaflets 550 that are radially expanded (as shown in FIG. 1A) during systole and radially collapsed towards the central axis during diastole. The frame 545 can include a plurality of convex arms extending from the shaft 519. The convex arms can ensure that the flow optimizer 540 maintains a substantially convex cup shape when expanded. This can advantageously ensure that no blood pools between the anchor assembly 510 and the flow optimizer 540 during systole. Further, as shown in FIG. 6, the distal end 561 of the shaft 519 can have detents cut therein to avoid interaction with the collapsed leaflets 550 during diastole.

During diastole, when blood flows from the right atrium into the right ventricle through the tricuspid valve under atrial contraction, the atrioventricular hemodynamic pressure gradient opens the tricuspid valve leaflets (similar to as shown in FIGS. 7A-8C). The atrioventricular hemodynamic pressure gradient can collapse the leaflets 550 of flow optimizer 540 towards the center axis of the frame 545, such that the three-dimensional volume and cross sectional area of the flow optimizer 540 can be reduced, thereby allowing blood to flow unrestricted into the ventricle around the flow optimizer 540. During systole (i.e., ventricular contraction), when the tricuspid valve leaflets coapt around the flow optimizer 540, the ventricular hemodynamic pressure can inflate the leaflets 550 to their full or partial three-dimensional volume, which can be sufficient to close the tricuspid valve regurgitant orifice and reduce or prevent blood flow into the right atrium.

Advantageously, the device 500 can ensure that the pressure gradient across the tricuspid valve after implantation remains low, such as less than 3 or less than 2 mmHg.

Device 500 can be loaded, for example, within an intravascular catheter and delivered to the right atrium and into the tricuspid valve either via transfemoral access through the IVC, or via right internal jugular vein access of the IVC.

Another embodiment of a tricuspid valve support device 700 is shown in a deployed configuration (and with leaflets collapsed) in FIGS. 7A-8C. The support device 700 is similar to support device 500 and includes an anchoring mechanism 710 with a plurality of arms 715*a-c* that are radially disposed around and from an inner core 721 (and that can be locked with screws 722*b,c*). Further, the shaft 719, which is fixed to the flow optimizer 740, can be configured to slide and rotate axially relative to the anchoring mechanism 710 (similar to device 500), and the leaflets of the flow optimizer can expand and collapse during systole and diastole, respectively.

Unlike device 500, however, the shaft 719 and flow optimizer 740 of device 700 is configured so as to also be adjustably positioned off-axis relative to the anchoring mechanism 710 (i.e., can be configured to tilt). This tilting adjustment can allow for precise angular positioning of the flow optimizer 740 relative to the native tricuspid valve. To enable adjustable angular positioning of the flow optimizer 740, the device 700 (e.g., the core 721) includes a ball 771 positioned within a socket 773. The ball 771 includes a lumen 775 through which the shaft 719 extends, and the shaft 719 can slide or rotate within the central lumen 775. Further, the ball 771 can rotate within the socket 773, thereby allowing placement of the flow optimizer 740 off-axis relative to the anchoring mechanism 710 (see FIGS. 8A-8C). An angled ledge 779 on the lumen 751 of the core 721 can prevent the flow optimizer 740 from extending at too large of an angle relative to the anchoring mechanism 710 (e.g., the angle of the axis of the anchoring mechanism 710 relative to the axis of the flow optimizer 740 can be limited to less than 45 degrees, such as less than 35 degrees, such as less than 25 degrees.

Once the flow optimizer 740 and anchoring assembly 710 are at the desired relative positions, the flow optimizer 740 and anchoring assembly 710 can be locked in position relative to one another via activation of screws 777, 779. The screws 777, 779 can engage with (and rotate within) threaded holes in the inner core 721. The threaded holes can extend at an angle relative to the longitudinal axis of the device (e.g., at an angle of 5-45 degrees, such as 10-30 degrees). The screws 777, 779 can be configured to extend through the holes until they engage with the ball 771. Upon engagement by a first amount, the position of the ball 771 can be fixed, thereby fixing the angular position of the anchoring assembly 710 relative to the flow optimizer 740. At this first amount, the shaft 719 can still be permitted to move (e.g., axially slide and rotate) within the lumen 775 (e.g., for axial or rotational positioning of the flow optimizer 740 relative to the anchoring assembly 710). Upon tightening the screws 777 by a second additional amount, the ball 771 can push against the shaft 719 and thereby prevent the shaft 719 from moving within the lumen 775 and fixing the axial and rotational position of the flow optimizer 740 relative to the anchoring assembly 710.

FIGS. 16A-16D show another embodiment of a tricuspid valve support device 1600. The device 1600, similar to device 700, includes a shaft 1619 and flow optimizer 1640 that are configured to be positioned off-axis relative to the anchoring mechanism 1610 (i.e., can be configured to tilt). Like device 700, the device 1600 includes a ball 1671 positioned within a socket 1673. Unlike device 700, however, device 1600 includes an annular lock 1662 configured to fit within the inner core 1621. The annular lock 1662 can include threaded grooves 1664 along the outside thereof configured to engage with threaded grooves 1666 on an inner surface of the inner core 1621. In use, the annular lock 1662 can be positioned in a proximal configuration (shown in FIGS. 16A-16B) such that the flow optimizer 1640 is free to tilt relative to the anchoring assembly 1610. Once the flow optimizer 1640 and anchoring assembly 1610 are at the desired relative positions, the flow optimizer 1640 and anchoring assembly 1610 can be locked in positioned relative to one another via activation of the annular lock 1662. To do so, the annular lock 1662 can be rotated within the inner core 1621, resulting in the annular lock 1662 moving distally towards the ball 1671 and into a distal configuration (shown in FIG. 16C). Upon engagement with the ball 1671 by a first amount, the position of the ball 1671 can be fixed, thereby fixing the angular position of the anchoring assembly 1610 relative to the flow optimizer 1640. At this first amount, the shaft 1619 can still be permitted to move (e.g., axially slide and rotate) within the lumen 1675. Upon further rotation of the annular lock 1662 distally, the ball 1671 can push against the shaft 1619 and thereby prevent the shaft 1619 from moving within the lumen 1675 and fix the axial and rotational position of the flow optimizer 1640 relative to the anchoring assembly 1610.

Figure 17E:
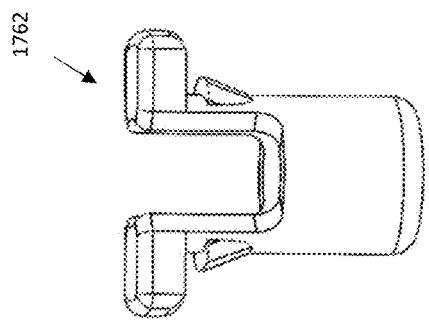
FIG. 17E is a perspective view of the annular lock of the device of FIG. 17A.
Figure 17B:
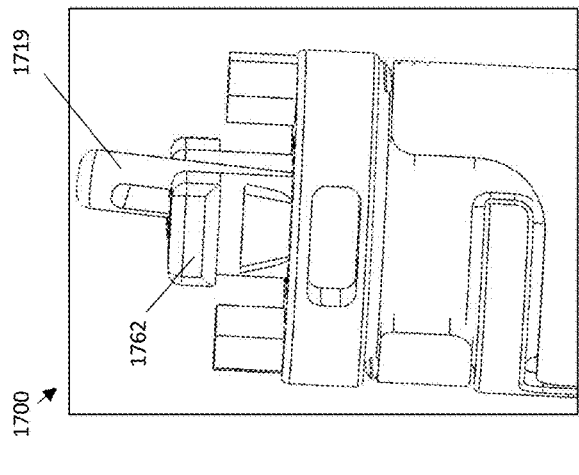
FIG. 17B is a perspective view of the valve support device of FIG. 17A with the annular lock in the proximal configuration.
Figure 17D:
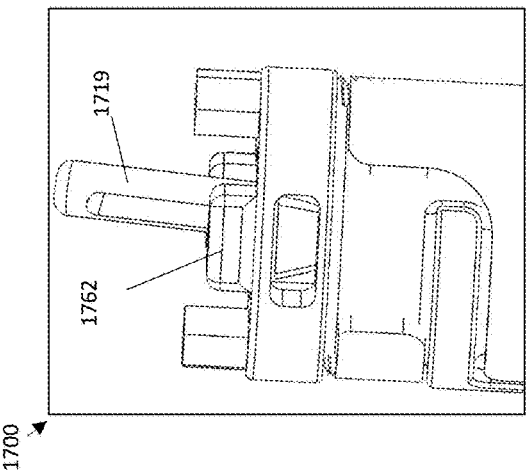
FIG. 17D is a perspective view of the valve support device of FIG. 17A with the annular lock in the distal configuration.
Figure 17A:
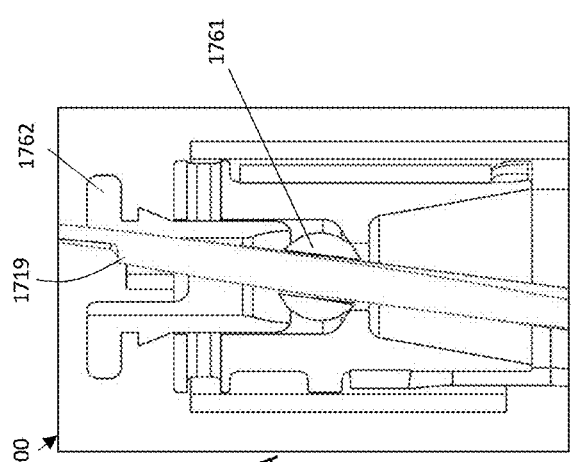
FIG. 17A is a cross-sectional view of the proximal end of a valve support device with an annular lock in a proximal (unlocked) configuration.
Figure 17C:
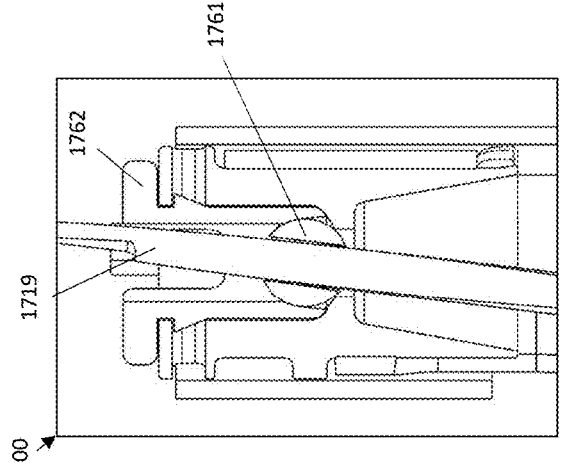
FIG. 17C is a cross-sectional view of the valve support device of FIG. 17A with the annular lock in the distal (locked) configuration.

FIGS. 17A-17E show another embodiment of the proximal end of a tricuspid valve support device 1700. The device 1700, similar to device 1600, includes an annular lock 1762 to lock the tilting position of flow optimizer relative to the anchor assembly. The annular lock 1762, in contrast to annular lock 1662, can be a snap fit lock (rather than a screw lock). As shown in FIGS. 17A-17B, the annular lock 1762 can be positioned in a proximal configuration in which the lock 1762 is not engaged with the ball 1761 and the shaft 1719 is free to tilt (and/or rotate or move axially). As shown in FIGS. 17C-17D, the annular lock 1762 can be pushed distally (i.e., rather than rotated) to the distal configuration in which the lock 1762 engages with the ball 1761 to lock the position of the shaft 1719.

Advantageously, the adjustability of the arms of the anchoring mechanisms described herein (e.g., shape and rotational position) in combination with the adjustability of the position of the anchoring mechanism relative to the flow optimizer as described herein (e.g., rotational, angular, and/or axial) provides for precise alignment of the device relative to the native tricuspid valve. The device can be fully integrated with the tricuspid valve and annulus, moving harmonically and ergonomically in systolic and diastolic phases without impeding the atrium or ventricle. Additionally, this adjustability can be performed live by the operator, thereby allowing immediate assessment and adjustments before permanently implanting the device, improving treatment outcome. Similarly, the amount of seal (partial or total) within the tricuspid valve provided by the flow optimizers described herein can be adjusted intraprocedurally (via tilt, rotation, and axial adjustment of the flow optimizer relative to the anchoring mechanism) and can be based on assessment or monitoring of the patient's RV functionality and pulmonary artery pressure.

Figure 9A:
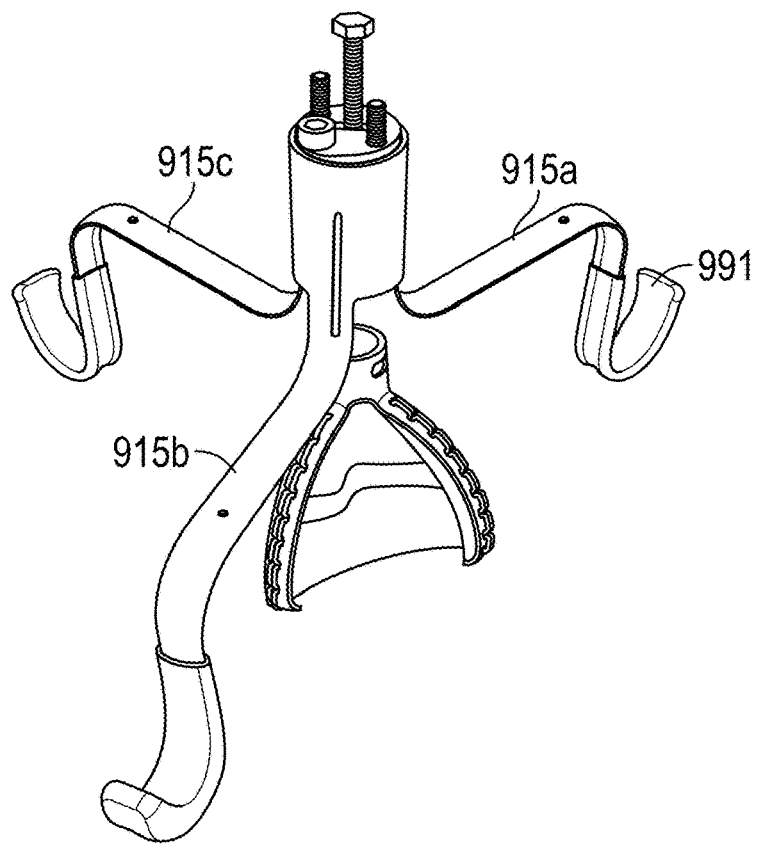
FIG. 9A is a perspective view of a valve support device having a covering on the outer tips of the anchoring arms.
Figure 9B:
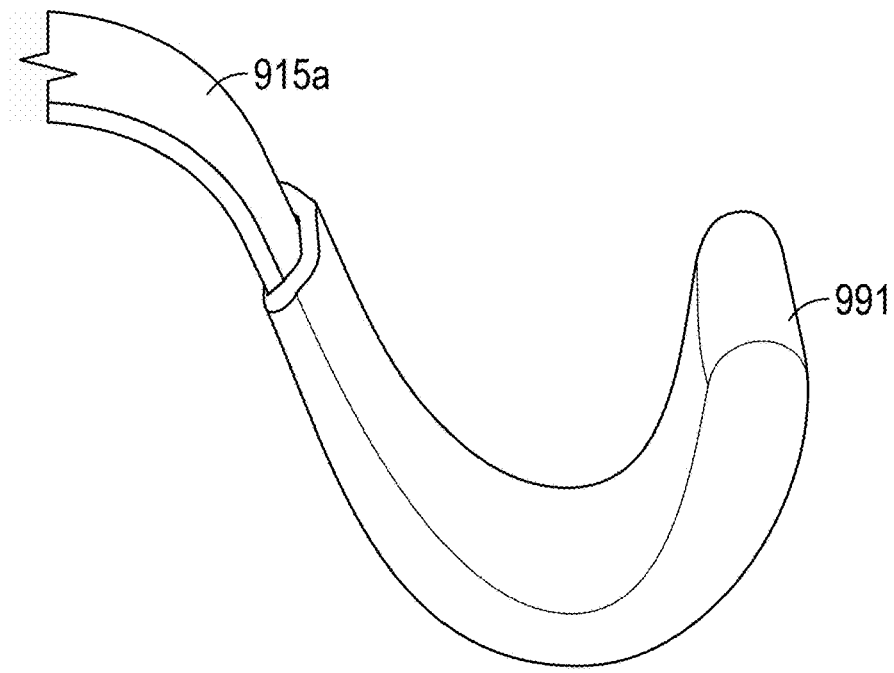
FIG. 9B is a close-up view of the outer tips of the anchoring arms of the device of FIG. 9A.

Referring to FIGS. 9A-9B, in some embodiments, the anchoring arms 915*a-c* of any of the devices described herein (e.g., arms 515*a-c* and 715*a-c*) can include a covering 991 on the outer tips thereof. The covering 991 can be made, for example, of polyethylene terephthalate fabric. In some embodiments, the covering 991 can extend only around the outer portion of the arms 915*a*, such as along the outer 10-40%, such as 25-35% of the arms 915*a-c*. The covering 991 can advantageously enhance endothelial growth and subsequent encapsulation of the outer tips of the anchors 915*a-c* (e.g., at the annulus). The remaining portions of the arms 915*a-c* can remain uncovered, thereby helping to prevent thrombus formation during use.

Figure 15A:
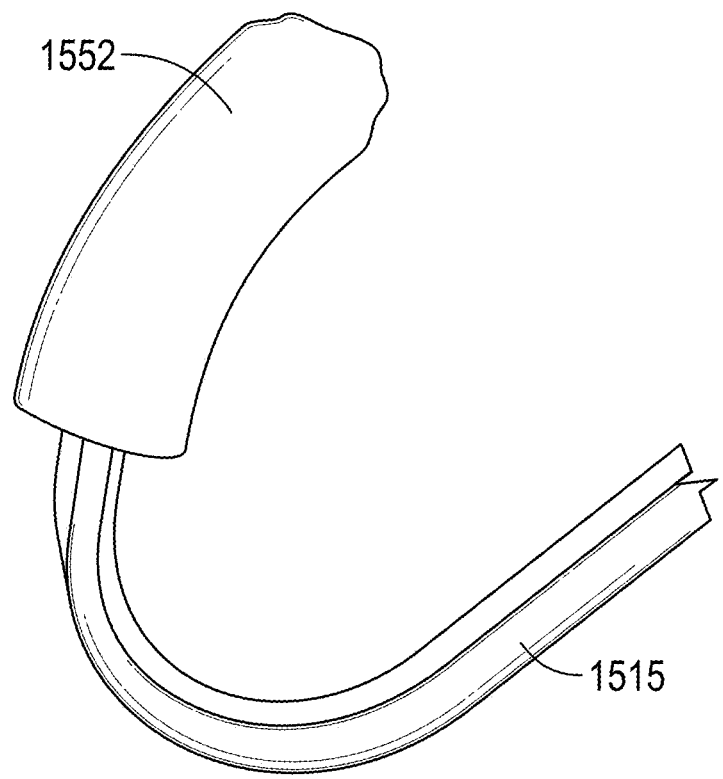
FIG. 15A shows the distal tip of a valve support device anchoring arm with a cushion thereon (outer sleeve is removed for clarity).
Figure 15B:
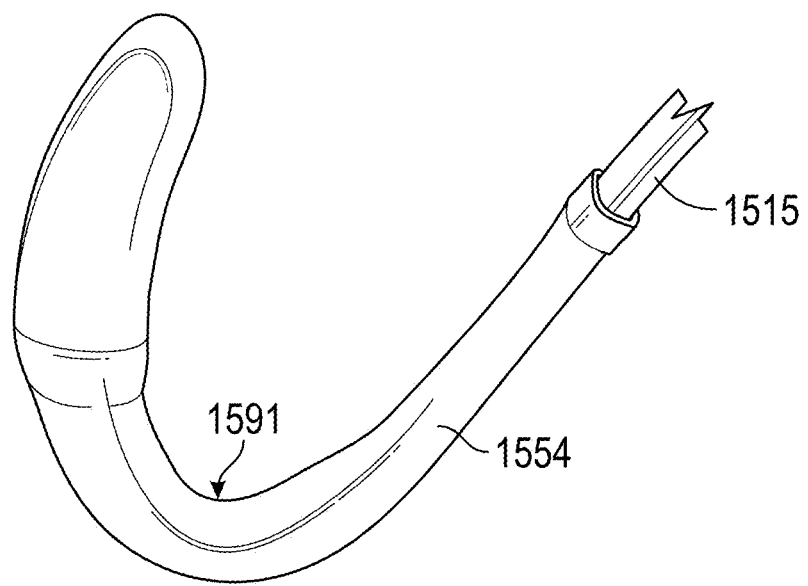
FIG. 15B shows the distal tip of FIG. 15A with the sleeve thereover.

Referring to FIGS. 15A-15B, in some embodiments, the covering 1591 (e.g., covering 991) can include a cushion 1552 and a sleeve 1554. The cushion 1552 can extend, for example, only on the distal tip of each arm 1515, such as along the portion of the arms 1515 that hooks backwards (e.g., within the outer 10% of the arm 1515). The sleeve 1554 can be placed over the cushion 1552 and the arms 1515 and can extend the full length of the covering 1591. The cushion 1552 can advantageously aid in making the tips of the arms 1515 atraumatic. In some embodiments, the cushion 1552 can be made of a plurality of layers of fabric, such as 3-10, such as 4-8 layers of fabric that are sealed together. For example, the cushion 1552 can be made of layers of polyethylene terephthalate (PET) fabric. In some embodiments, the cushion 1552 can be made of a single piece of foam.

The leaflets for any of the devices described herein can be made of a material that is impermeable to blood cells and, preferably, impermeable to blood fluids (e.g., aqueous solutions). For example, the leaflets can be formed from any suitable biocompatible material including, for example, woven or nonwoven polymer fabrics or sheets and/or biological tissue harvested from animals (e.g., bovine, porcine, and equine) or humans. Suitable biological tissue includes, for example, tissue obtained from the pericardial sac of the donor animal and/or human. In some embodiments, the leaflets can be made of a composite polymer material. The composite material can be made of a two-dimensional woven (or braided or knitted) fabric (e.g., a PET fabric sheet) or of a three-dimensional thermo-formed fabric (e.g., a PET fabric shape). The fabric layer can advantageously carry the cyclic fatigue loading exerted on the leaflets by the cardiac cycle's hemodynamic flow. The porosity of the fabric can be engineered to allow coating it with a biocompatible and anti-thrombus coating, such as polyurethane (PU) or polyurethane-silicone (PU-Sil), without significantly affecting the fabric's flexibility. In some embodiments, the coating can be applied in liquid form to the fabric using standard coating manufacturing processes (i.e. dipping, spraying, electro-spinning). The coating can fully cover and isolate the fabric from the blood stream. In some embodiments, the final composite material (e.g., PET+PU or PET+PU-Sil) can provide high fatigue resistance due to the woven fabric substrate and strong chemical stability due to the coating.

The leaflets can be sutured or attached with other standard fastening methods (e.g. adhesives) on the arms of the frame (e.g., frame 545). Additionally and/or alternatively, the leaflets can be molded in the desired three dimensional shape as a single sub-assembly mountable on the frame.

Figure 10A:
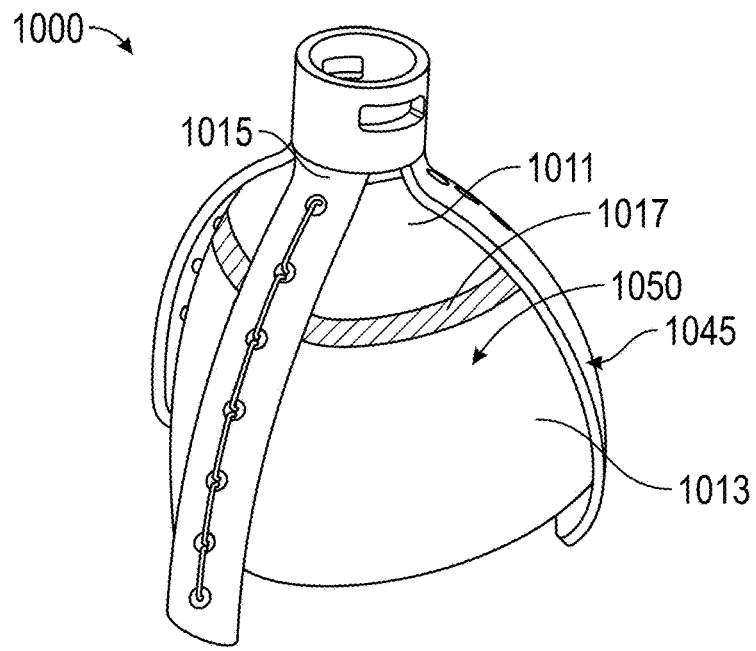
FIG. 10A is a perspective view of a flow optimizer with multi-layered leaflets in the expanded configuration.
Figure 10B:
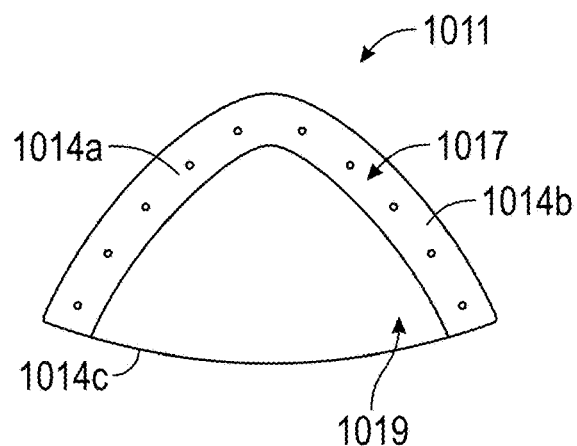
FIG. 10B shows a top layer of the leaflets of FIG. 10A.
Figure 10C:
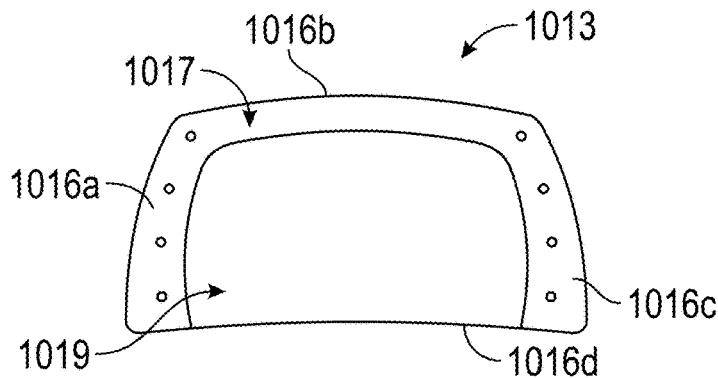
FIG. 10C shows a bottom layer of FIG. 10B.

Referring to FIGS. 10A-10C, in some embodiments, the leaflets 1050 (which can be any of the leaflets described herein) of device 1000 can be composed of two circumferential layers. That is, each leaflet can have a top layer 1011 (positioned towards the apex 1015 at the atrial end of the frame 1045) and a bottom layer 1013 (positioned towards the ends or tips of the convex frame arms at the ventricular end of the frame 1045). The top layer 1011 can be substantially triangular in shape while the bottom layer 1013 can be substantially rectangular or quadrilateral in shape. The layers 1011, 1013 can be in a radially overlapping configuration with the bottom layer 1013 positioned radially outwards of the top layer 1011. During systole, the leaflets 1050 can be substantially convex (as shown in FIG. 10A), and layers 1011 and 1013 can be sealed against and/or in contact with one another.

As shown in FIGS. 10B-10C, each individual leaflet layer 1011, 1013 can include a rim 1017 and a membrane 1019. The membrane 1019 can include a thin layer of polymeric material, such as polyurethane-silicone. The rim 1017 of the top layer 1011 can extend along first and second edges 1014*a,b* (closest to the apex 1015) while leaving the third edge 1014*c* (the ventricular-most edge) without a rim. Similarly, the rim 1017 of the bottom layer 1013 can extend along first, second, and third edges 1016*a,b,c* while leaving the fourth edge 1016*d* (the ventricular-most edge) without a rim. The rim 1017 can be made, for example, of a fabric, such as polyethylene terephthalate fabric. In some embodiments, the rim 1017 can have a coating thereover, such as a coating of polyurethane and/or silicone. Further, the rim 1017 can be thicker and/or have greater stiffness than the membrane 1019.

Referring to FIGS. 11A-11C, during diastole, when blood flows from the right atrium into the right ventricle, the hemodynamic pressure gradient can cause the leaflets 1050 of device 1000 to collapse towards the center axis of the frame 1045 and/or to become concave (the concave leaflets 1050 are shown in FIG. 11A). As shown in FIGS. 11B-11C, because the overlapping layers 1013, 1011 have varying stiffness (i.e., due to the position and size of the rims 1017), the top layer 1011 can collapse first, thereby leaving a gap 1018 between the top layer 1011 and the bottom layer 1013. That is, the stiffness of the rim 1017 along the edges 1016a,b,c of the bottom layer 1013 can hold the bottom layer 1013 radially outwards longer than the unrimmed overlapping bottom edge 1014c of the top layer 1011. Having the layers 1011, 1013 move sequentially (e.g., the top layer 1011 move radially inwards before the bottom layer 1013) can allow blood to flow through the gap 1018, minimizing the potential areas for blood stagnation and thus preventing thrombus formation in or around the leaflets 1050. Additionally, the sequential collapse can help minimize obstruction of atrio-ventricular flow during the diastolic phase by reducing the effective orifice area (e.g., can help maintain the gradient of less than 3 mmHg, such as less than 2 mmHg post-implantation). In other embodiments, the top and bottom layers 1011, 1013 can be configured so as to collapse simultaneously.

Figure 12A:
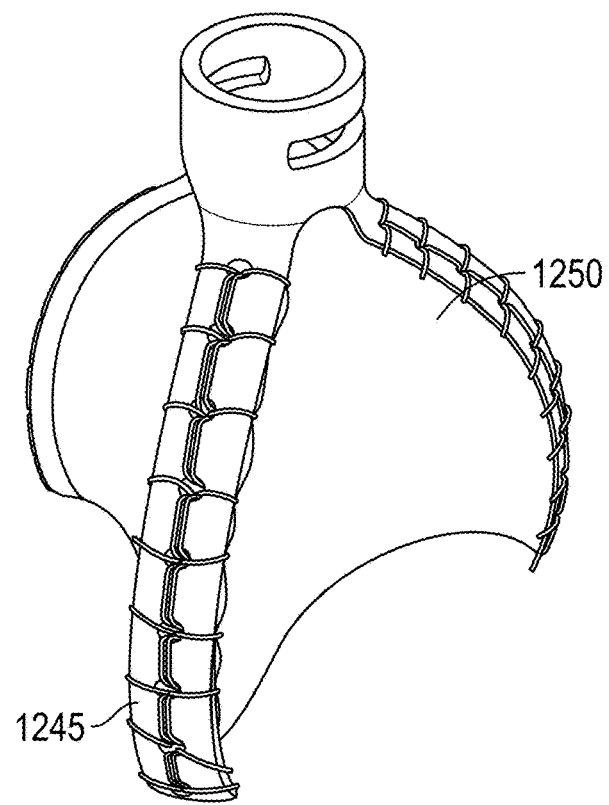
FIG. 12A is a perspective view of a flow optimizer with leaflets sewn to the frame in a first stitch pattern.
Figure 12B:
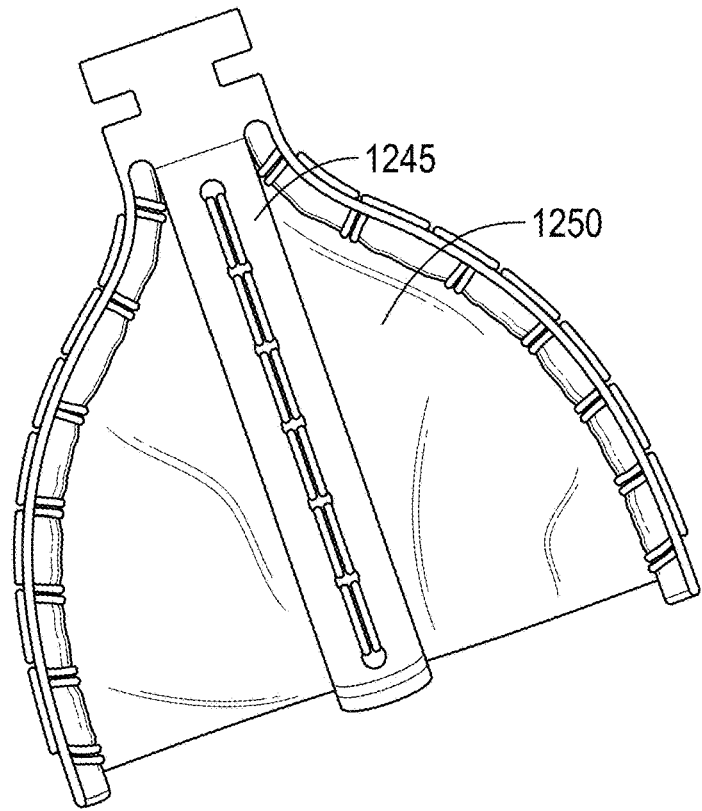
FIG. 12B is a perspective view of a flow optimizer with leaflets sewn to the frame in a second stitch pattern.

Referring to FIGS. 12A-12B, the leaflets 1250 (which can be any of the leaflets described herein) can be sewn to the frame 1245 along the rims (e.g., the rims 1017, 1019 along edges 1014b,c and 1016a,b,c of FIGS. 10A-10C). The stitches can be parallel with the rims, which can advantageously reduce the impact on blood flow and reduce the risk of thrombosis. In some embodiments, the stitches can be positioned through predrilled (e.g., laser cut) holes to ensure alignment of the components when sewn together. The stitches can be wrapped around the arms of the frame 1245 (as shown in FIG. 12A) or extend only in direction parallel to the arms of the frame 1256 (as shown in FIG. 12B).

Figure 13A:
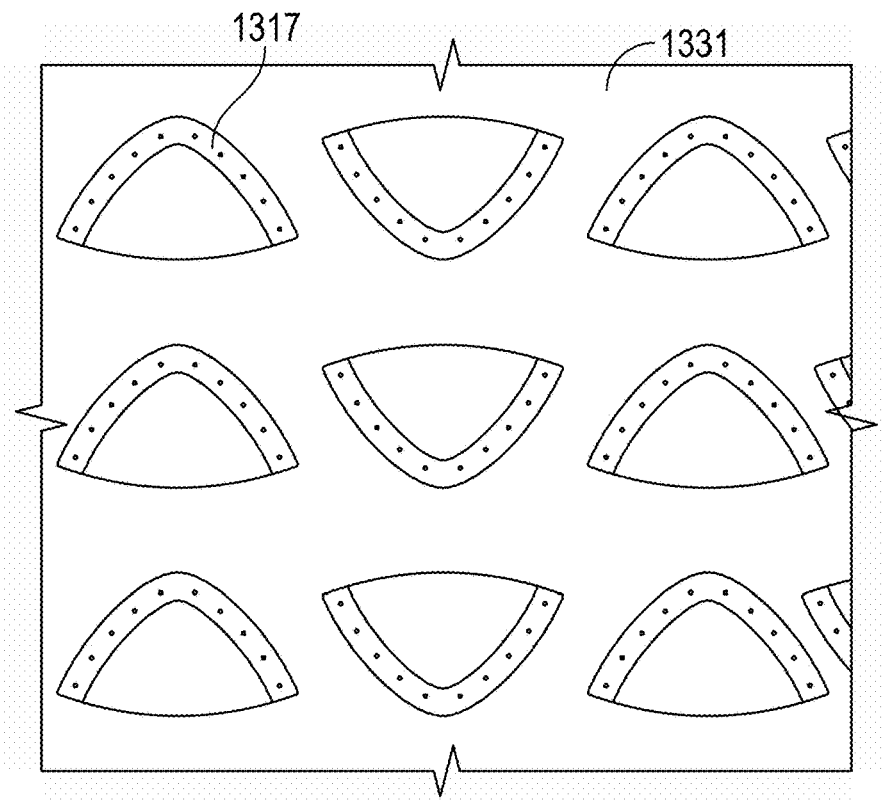
FIG. 13A shows a pattern for cutting a top layer of leaflets.
Figure 13B:
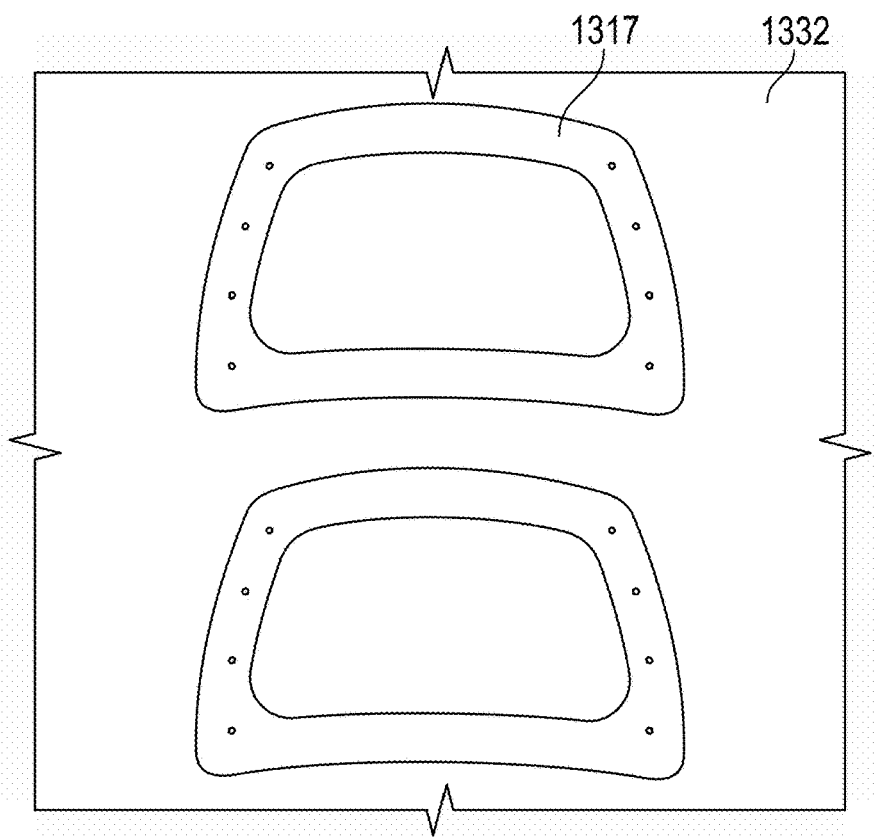
FIG. 13B shows a pattern for cutting a bottom layer of leaflets.

Referring to FIGS. 13A-13B, an exemplary method of manufacturing leaflets includes:
1) Obtaining a panel 1331, such as polyethylene terephthalate fabric coated with polyurethane and silicone. The panel 1331 can be, for example, 40 μm thick.
2) Laying the panel 1331 on a tray, such as a borosilicate glass tray.
3) Laser cutting the pattern of the top leaflets (as shown in FIG. 13A) into the panel 1331.
4) Removing the center portion of the top leaflets from the panel 1331, leaving only the rims 1317.
5) Repeating steps 1-5 for the bottom leaflets (the patterned panel 1332 for which is shown in FIG. 13B).
6) Coating the entire surface of the panels 1331, 1332, including the cut-out portions, with one layer of a coating, such as a coating of polyurethane and silicone. The coating can be, for example, 20 μm thick. The coating can create the membrane between the rims 1307.
7) Repeating step 7 to apply additional coating layers as required to reach a thickness of the rim and membrane as desired.
8) Cutting the completed leaflets away from the panels 1331, 1332.

Figure 14A:
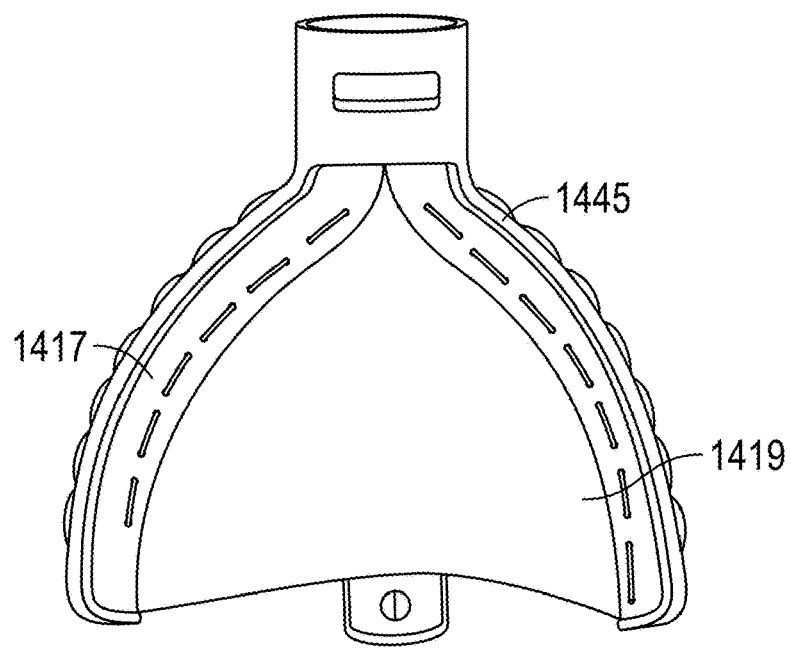
FIG. 14A is a perspective view of a flow optimizer with single-layer leaflets.
Figure 14B:
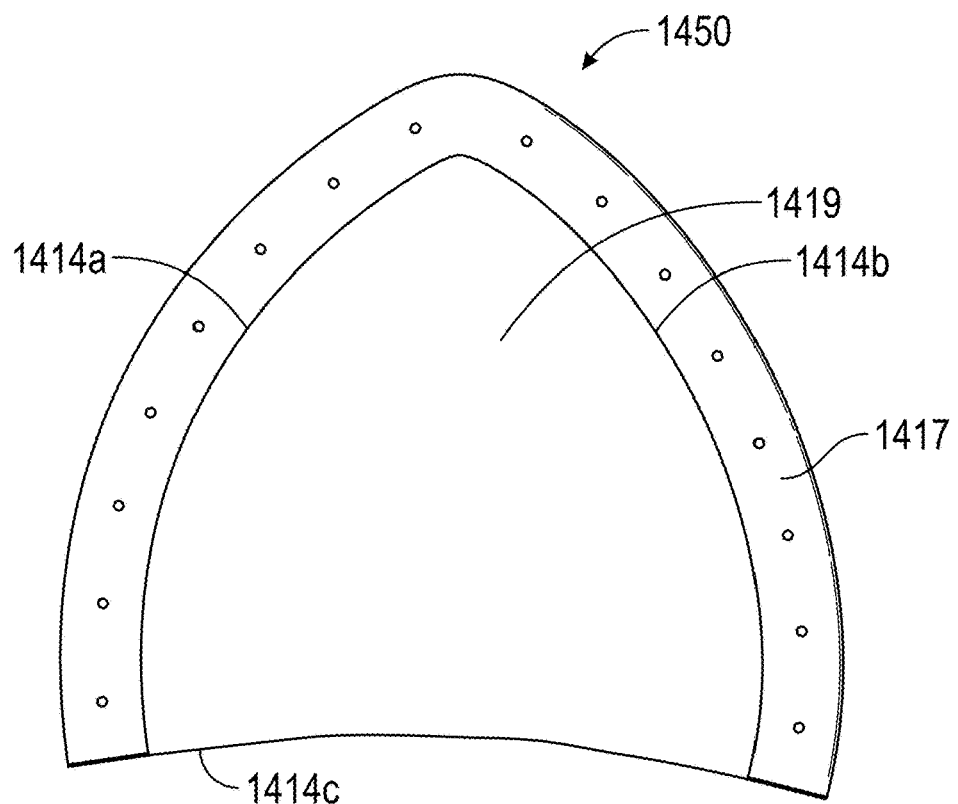
FIG. 14B shows a leaflet of the flow optimizer of FIG. 14A.

Referring to FIGS. 14A-14B, in some embodiments, the leaflets 1450 (which can be used as part of any of the flow optimizers described herein) can be composed of a single circumferential layer. Each leaflet 1450 can have a substantially triangular shape. Additionally, each leaflet 1450 can have a rim 1417 and a membrane 1419 as described above with respect to leaflets 1050. Similar to the top layer 1011, the rim 1417 can extend along first and second edges 1414a,b (towards apex 1415) while leaving a third edge 1414c (the ventricular-most edge) without a rim. The leaflets 1450 can be made with the same process as described above with respect to the dual circumferential layers of leaflets with the exception of step 5 (i.e., without manufacturing the bottom leaflets). In use, during diastole, when blood flows from the right atrium into the right ventricle, the hemodynamic pressure gradient can cause the leaflets 1450 to collapse towards the center axis of the frame 1445. Because the membrane 1419 is thinner than the rim 1417 (e.g., has a thickness than is less than 75%, such as less than 60%, such as less than 55%, such as less than or equal to 50% of the rim), the membrane 1419 can advantageously collapse quickly during diastole (and similarly expand quickly during systole).

In some embodiments, the ratio of the cross-sectional area of the device relative to the area of the tricuspid valve annulus during diastole can be less than 0.4, such as less than 0.3, such as less than or equal to 0.26. Having a low ratio of cross-sectional area relative to the tricuspid valve annulus can advantageously help ensure that the pressure gradient across the valve remains low (such as less than 3 or less than 2 mmHg).

In some embodiments, some or all of the devices described herein can be echogenic and/or radiopaque, allowing for intraprocedural visualization.

Advantageously, the devices described herein can be placed even in the presence of a pacemaker lead. Additionally, the devices described herein can allow for the crossing of ancillary devices from the right atrium to the right ventricle without interfering with the device functionality.

In some embodiments, the cross-section of an expanded flow optimizer as described herein can be substantially round or oval (or a convex triangle) while the cross-section of the unexpanded flow optimizer can be triangular (or a concave triangle).

The devices described herein can additionally or alternatively include any of the features described in PCT Publication No. WO/2018/119192, titled "Heart Valve Support Device and Methods for Making and Using the Same," the entirety of which is incorporated by reference herein.

It should be understood that the devices and methods described herein can, additionally or alternately to being used in the tricuspid valve, be used in other heart valves, such as the mitral valve or the aortic valve.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A device for assisting with functioning of a tricuspid valve of a heart, comprising:
   a shaft;
   a flow optimizer fixedly connected to a distal end of the shaft;
   an anchoring mechanism comprising a core having a socket therein; and
   a ball positioned within the socket, the ball having a lumen therein through which the shaft is configured to extend, wherein the ball is configured to rotate within the socket so as to tilt the shaft relative to a central axis of the anchoring mechanism.

2. The device of claim 1, wherein the shaft is configured to slide axially and rotate within the lumen.

3. The device of claim 1, wherein the core comprises an angled ledge configured to limit an angle of the flow optimizer relative to the anchoring mechanism.

4. The device of claim 3, wherein the angle is less than 45 degrees.

5. The device of claim 1, further comprising a locking mechanism configured to lock an angle of tilt of the flow optimizer relative to the anchoring mechanism.

6. The device of claim 5, wherein the locking mechanism is further configured to lock an axial and rotational position of the flow optimizer relative to the anchoring mechanism.

7. The device of claim 5, wherein the locking mechanism comprises one or more screws configured to extend through the core and engage the ball.

8. The device of claim 5, wherein the locking mechanism comprises an annular lock configured to fit between the core and the ball.

9. The device of claim 8, wherein the annular lock is configured to move axially between a proximal position in which the ball is configured to rotate and a distal position in which the ball is fixed.

10. The device of claim 8, wherein the annular lock is a snap fit lock.

11. The device of claim 8, wherein the annular lock includes threaded grooves configured to mate with threaded grooves on an inner surface of the core.

12. The device of claim 1, wherein the flow optimizer comprises a frame and a plurality of leaflets attached to the frame.

13. The device of claim 12, wherein the plurality of leaflets are configured to expand to an expanded configuration during systole to block a flow of blood around the flow optimizer and to collapse to a collapsed configuration during diastole to allow a flow of blood around the flow optimizer.

14. The device of claim 1, wherein the anchoring mechanism further comprises a plurality of anchoring arms extending radially away from the core.

15. A method of assisting with functioning of a tricuspid valve of a heart, comprising:
   inserting a tricuspid valve device into a native tricuspid valve, wherein the tricuspid valve device comprises a shaft, a flow optimizer, and an anchoring mechanism;
   fixing the anchoring mechanism at commissures leaflets of the native tricuspid valve; and
   tilting the shaft relative to a central axis of the anchoring mechanism so as to position the flow optimizer at a desired angular position within the native tricuspid valve.

16. The method of claim 15, wherein tilting the shaft comprises rotating a ball within a socket of the tricuspid valve device.

17. The method of claim 15, further comprising:
   during diastole, reducing a cross-sectional area of the flow optimizer to allow hemodynamic flow around and through the flow optimizer; and
   during systole, increasing a cross-sectional area of the flow optimizer to seal an orifice of the native tricuspid valve.

18. The method of claim 15, further comprising axially moving the shaft relative to the anchoring mechanism after fixing the anchoring mechanism so as to position the flow optimizer at a desired axial position within the native tricuspid valve.

19. The method of claim 15, further comprising rotating the shaft relative to the anchoring mechanism after fixing the anchoring mechanism so as to position the flow optimizer at a desired rotational position within the native tricuspid valve.

20. The method of claim 15, further comprising locking the flow optimizer at the desired angular position with a locking mechanism.

21. The method of claim 20, wherein the locking mechanism further locks an axial and rotational position of the flow optimizer relative to the anchoring mechanism.

22. The method of claim 20, wherein the locking mechanism comprises one or more screws configured to extend through the core and engage with the ball.

23. The method of claim 20, wherein the locking mechanism comprises an annular lock configured to fit around the shaft.

24. The method of claim 23, wherein locking comprises distally moving the annular lock relative to the anchoring mechanism.

25. The method of claim 23, wherein locking comprises rotating the annular lock relative to the anchoring mechanism.

* * * * *